United States Patent
Moraitis

(10) Patent No.: US 10,780,097 B2
(45) Date of Patent: *Sep. 22, 2020

(54) USE OF CORTISOL IN ASSESSMENT AND PROPHYLACTIC TREATMENT OF HYPOKALEMIA ASSOCIATED WITH GLUCOCORTICOID RECEPTOR MODULATOR TREATMENT OF CUSHING'S SYNDROME PATIENTS

(71) Applicant: Corcept Therapeutics, Inc., Menlo Park, CA (US)

(72) Inventor: Andreas Moraitis, Menlo Park, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 30 days.

This patent is subject to a terminal disclaimer.

(21) Appl. No.: 16/109,585

(22) Filed: Aug. 22, 2018

(65) Prior Publication Data

US 2020/0000824 A1     Jan. 2, 2020

Related U.S. Application Data

(60) Provisional application No. 62/693,318, filed on Jul. 2, 2018.

(51) Int. Cl.
| | | |
|---|---|---|
| *A61K 31/567* | (2006.01) |
| *G01N 33/74* | (2006.01) |
| *A61P 5/10* | (2006.01) |
| *A61P 3/10* | (2006.01) |
| *A61P 5/06* | (2006.01) |
| *A61K 45/06* | (2006.01) |

(52) U.S. Cl.
CPC ............. *A61K 31/567* (2013.01); *A61P 3/10* (2018.01); *A61P 5/06* (2018.01); *A61P 5/10* (2018.01); *G01N 33/743* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 9,216,221 B2 | 12/2015 | Newell-Price | |
| 9,877,937 B2 | 1/2018 | Hammer et al. | |
| 10,314,850 B1 | 6/2019 | Moraitis | |
| 2010/0249081 A1* | 9/2010 | Gupta | A61K 31/404 514/171 |
| 2010/0261693 A1* | 10/2010 | Ulmann | A61K 31/567 514/179 |
| 2014/0170768 A1 | 6/2014 | Ehrenkranz | |

FOREIGN PATENT DOCUMENTS

| | | |
|---|---|---|
| WO | 2016197116 A1 | 12/2016 |
| WO | 2017127448 A1 | 7/2017 |

OTHER PUBLICATIONS

Colao et al., "Managing hyperglycemia in patients with Cushing's disease treated with pasireotide: medical experts recommendations," Pituitary (2014) 17:180-186.*
Fassanacht et al., "Merits and pitfalls of mifepristone in Cushing's syndrome," European Journal of Endocrinology (2009) 160 1003-1010.*
Krone et al., "Cortisol," UCSF Benioff Children's Hospital (Dec. 11, 2011).*
Auchus, et al., "MON-450: Predicting and Managing Hypertension and Hypokalemia in Cushing Syndrome during Mifepristone Therapy," The Endocrine Society's 94th Annual Meeting and Expo, Jun. 23-26, 2012—Houston, TX, 2 pages, http://press.endocrine.org/doi/abs/10.1210/endo-meetings.2012.AHPAA.4.MON-450.
Banerjee, et al., "Mifepristone Treatment of Cushing's Syndrome in a Pediatric Patient," Pediatrics, (Nov. 2015), vol. 136, No. 5, pp. e1377-e1381.
Bilgin, et al., "Treatment of severe psychosis due to ectopic Cushing's syndrome," J. Endocrinol. Invest. 30:776-779, 2007.
Castinetti, et al., "Medical Treatment of Cushing's Syndrome: Glucocorticoid Receptor Antagonists and Mifepristone," Neuroendocrinology (2010), 92(suppl 1):125-130.
Christy, et al., "Pathogenesis of Hypokalemic Alkalosis in Cushing's Syndrome," The New England Journal of Medicine, (Nov. 30, 1961), 265(22):1083-1088.
Chu, et al., "Successful Long-Term Treatment of Refractory Cushing's Disease with High-Dose Mifepristone (RU 486)," J. Clin. Endocrinol. Metab., (2001), 86(8):3568-3573.
Fleseriu, et al., "Mifepristone, a Glucocorticoid Receptor Antagonist, Produces Clinical and Metabolic Benefits in Patients with Cushing's Syndrome," J. Clin. Endocrinol. Metab., Jun. 2012, 97(6):2039-2049.
Kikuchi, et al., "Periodic hypokalemia associated with cyclic Cushing's syndrome," CEN Case Rep (2014) 3:80-85.

(Continued)

*Primary Examiner* — Jared Barsky
(74) *Attorney, Agent, or Firm* — Kilpatrick Townsend & Stockton LLP

(57) ABSTRACT

This invention provides new methods for a) identifying Cushing's Syndrome patients at high risk of developing hypokalemia during glucocorticoid receptor modulator (GRM) treatment, and b) for prophylactically treating such patients to prevent, or reduce the severity of, hypokalemia. Patients at such high risk may be identified prior to their developing hypokalemia. Such a patient may be an adult patient with endogenous Cushing's Syndrome having type 2 diabetes mellitus or glucose intolerance to control hyperglycemia secondary to hypercortisolism. Patients may be identified by an above-threshold level of ACTH or cortisol in a patient sample taken post-GRM administration or pre-GRM administration, respectively. Upon identifying such a patient prior to the development of low potassium, the present methods provide for prophylactically treating the patient by administration of one or more hypokalemia treatments concurrently with an increased dose of GRM or with an initial dose of GRM to prevent hypokalemia.

7 Claims, 4 Drawing Sheets

(56) References Cited

OTHER PUBLICATIONS

Minami, et al., "A case of ACTH-dependent Cushing's syndrome whose definite diagnosis is difficult because of the fact that pituitary tumor is observed in the image examination while endocrine examination conforms with ectopic ACTH production syndrome," The 16th Annual Meeting of the Japanese Society for Hypothalamic and Pituitary Tumors Proceeding, Japanese Endocrine Society Journal vol. 82 Suppl. Jun. 2006, 14 pages.

Perogamvros, et al., "Simultaneous measurement of cortisol and cortisone in human saliva using liquid chromatography—tandem mass spectrometry: Application in basal and stimulated conditions," J. of Chromatography B, 877 (2009) 3771-3775.

Perogamvros, et al., "Measurement of salivary cortisol with liquid chromatography-tandem mass spectrometry in patients undergoing dynamic endocrine testing," Clinical Endocrinology (2010) 72:17-21.

Putignano, et al., "Salivary cortisol measurement in normal-weight, obese and anorexic women: comparison with plasma cortisol," European Journal of Endocrinology (2001) 145:165-171.

Torpy, et al., "Association of Hypertension and Hypokalemia with Cushing's Syndrome Caused by Ectopic ACTH Secretion," Ann. N.Y. Acad. Sci. 970:134-144 (2002).

Yamashita, et al., "Hypokalemia in Cushing's Disease," The 26th Annual Meeting of the Japanese Society for Hypothalamic and Pituitary Tumors Proceeding, Japan Endocrine Society Journal vol. 92 Suppl. HPT Jul. 2016, 9 pages.

"Comment on High Urinary Free Cortisol Excretion in a Patient with Psychogenic Polydipsia" Letters to the Editor, J. Clin. Endocrinology and Metabolism, 1998, 83(9):3378.

Moraitis et al., "Anticipating Hypokalemia in Patients With ACTH-Dependent Cushing Syndrome Treated With Mifepristone: Utilization of Cortisol and ACTH Levels to Identify At-Risk Patients", Poster SUN-460, In: Endocrine Society 2019 Annual Meeting, Mar. 2019.

PCT/US2019/038676 , "International Search Report and Written Opinion", dated Oct. 1, 2019, 13 pages.

Seow et al., "An Overlooked Cause of Hypokalemia", The American Journal of Medicine, vol. 130, No. 10, 2017, pp. e433-e435.

* cited by examiner

Figure 1. Comparison of Mean ACTH for Patients with Potassium of <3.5 mmol/L and of ≥3.5 mEq/L

Figure 2. Comparison of Mean Total Cortisol for Patients with Potassium of <3.5 mEq/L and of ≥3.5 mEq/L Figure 3. ROC Curve for Association between Total Serum Cortisol at Baseline and Early-Onset Hypokalemia. Numbers on the corners of the ROC curve correspond to Baseline (Day 1) Serum Cortisol levels.

Figure 4. ROC Curve for Association between ACTH at Day 14 and Subsequent Hypokalemia During Mifepristone Treatment

USE OF CORTISOL IN ASSESSMENT AND PROPHYLACTIC TREATMENT OF HYPOKALEMIA ASSOCIATED WITH GLUCOCORTICOID RECEPTOR MODULATOR TREATMENT OF CUSHING'S SYNDROME PATIENTS

RELATED APPLICATIONS

This application claims priority to U.S. Provisional Patent Application No. 62/693,318, filed Jul. 2, 2018, the contents of which are hereby incorporated by reference in the entirety for all purposes.

BACKGROUND

Cushing's syndrome, characterized by hypercortisolemia, is a condition involving a prolonged excess of circulating cortisol. Excess circulating cortisol leads to excess cortisol binding at the glucocorticoid receptor, which in turn causes a wide array of serious symptoms, including one or more of: hyperglycemia; hypertension; abdominal obesity and thin arms and legs; facial plethora; acne; hirsutism; proximal muscle weakness; bone loss; easy bruising; and red purple stripes across the body. Cushing's syndrome patients are at increased risk of hypertension, cardiac arrhythmias, atherosclerosis, and other cardiovascular disorders. Cushing's syndrome can be classified as exogenous Cushing's syndrome (caused by excess use of glucocorticoids drugs, such as prednisone, dexamethasone, and hydrocortisone), and endogenous Cushing's syndrome (caused by deregulatory abnormalities in the hypothalamus-pituitary-adrenal (HPA) axis). Endogenous Cushing's syndrome consists of Adrenocorticotropic hormone (ACTH)-independent Cushing's syndrome, characterized by an overproduction of cortisol in the absence of elevation of ACTH secretion; and ACTH-dependent Cushing's syndrome, characterized by excessive ACTH secretion.

ACTH-dependent Cushing's syndrome includes roughly 80% of patients having endogenous Cushing's syndrome and consists of two major forms: Cushing Disease and ectopic ACTH syndrome. The former is typically caused by a pituitary tumor and the latter is typically caused by a tumor outside the pituitary. Tumors may produce and secrete proteins and hormones such as corticotropin releasing hormone (CRH), ACTH, and/or cortisol, for example. Such proteins or hormones may not be active, or may only be partially active; see, e.g., Mathioudakis et al., Pituitary 15(4):526-532 (2012)). Correct differential diagnosis between the Cushing Disease and ectopic ACTH syndrome is important for endocrinologists to recommend transphenoidal surgery or appropriate imaging to identify source of the ectopic ACTH secretion. Thus, when a patient is identified as having a pituitary tumor (Cushing Disease), transsphenoidal surgery is indicated, and should be performed to remove (as much as is possible) the tumor. Patients identified as having an ectopic tumor (ectopic ACTH syndrome) should have appropriate imaging, and, if the source of the ectopic ACTH secretion is located, surgery should be performed to remove (as much as is possible) the tumor. However, some patients may not be candidates for surgery, or may fail surgery (e.g., not all the tumor may be removed). Patients that are not candidates for surgery, or who fail surgery, will likely benefit from treatments which block the effects of cortisol, such as treatment with a glucocorticoid receptor modulator (GRM).

Endogenous Cushing's syndrome patients may be treated by administration of a GRM. A GRM modulates the activity of a glucocorticoid receptor (GR). The GRM may be, for example, mifepristone. A GRM that antagonizes activation of the glucocorticoid receptor (GR) by GR ligands may also be termed a glucocorticoid receptor antagonist (GRA). Antagonistic activity of a GRM is typically effected by interfering with ligand binding to the GR. The main endogenous GR ligand is cortisol; artificial GR activating ligands include, e.g., dexamethasone, prednisone, and others. In the case of the GRM mifepristone, the GR modulation includes reducing the activity of the GR. Mifepristone administration, typically once-daily mifepristone administration, is used to treat Cushing's syndrome in patients, including ACTH-dependent Cushing's syndrome patients. Due to their elevated cortisol levels, Cushing's syndrome patients have an increased risk of developing hypokalemia, which occurs when cortisol levels are so high they overwhelm the enzyme (11-β hydroxysteroid dehydrogenase) that metabolizes cortisol to cortisone and so protects the mineralocorticoid receptor (MR) from cortisol, resulting in decreased potassium levels in the patients. Because GRM treatment raises cortisol levels even higher (even as the GRM reduces binding at GR), Cushing's syndrome patients treated with a GRM are at a significantly increased risk of developing hypokalemia. As hypokalemia is one of the most common adverse events associated with GRM treatment, it is important that the risk of developing hypokalemia among Cushing syndrome patients receiving GRM treatment be assessed and, when necessary, be addressed.

Hypokalemia (low potassium levels) is a serious condition, which can lead to cardiac arrhythmias and other cardiovascular disorders, and may be life-threatening. Potassium level is typically measured in a patient's blood stream, especially in a serum sample or plasma sample, according to methods known in the art. Normal potassium levels are typically between about 3.5 milliEquivalents per liter (mEq/L) to about 5.3 mEq/L. Patients with hypokalemia have low potassium levels (e.g., between about 2.5 mEq/L to below about 3.5 mEq/L); patients with potassium levels below about 2.5 mEq/L have severe hypokalemia. Patients suffering from hypokalemia may experience fatigue; edema; hypertension; muscle weakness, cramps, or muscle spasms; neurological problems including paresthesia and paralysis; renal problems such as polyuria, polydipsia, and nocturia; gastrointestinal disorders including abdominal cramps, constipation, nausea, and vomiting; long Q-T syndrome; cardiac palpitations and arrhythmias; and may be at risk of sudden cardiac arrest; and other symptoms and disorders. Hypokalemia, and in particular, severe hypokalemia, may require hospitalization for treatment and monitoring until normal potassium levels are regained. Hypokalemia may be treated by administration of a potassium supplement or a potassium sparing diuretic. Conversely, administering these medications to patients who are not hypokalemic and not at risk of developing hypokalemia has adverse implications: for instance, hyperkalemia can result and lead to significant dangers to the patients. This is an important reason why it would be very valuable to be able to predict the condition and ensure proper treatment of Cushing syndrome patients being treated or to be treated with GRM administration. However, means and methods for making such predictions are lacking in the art.

It would be advantageous to patients and treating physicians to be able to reliably predict which Cushing's syndrome patients are most likely to suffer from hypokalemia while receiving mifepristone for the treatment of Cushing's syndrome. However, reliable predictive markers have not been identified. For example, although cortisol may be measured in blood (e.g., serum or plasma), urine, and saliva, the levels measured in these ways differ and do not correlate with each other. Urinary free cortisol (UFC, a measure of cortisol in urine excreted over 24 hours) is used to diagnose Cushing's syndrome; however, UFC masks the daily cortisol variations by requiring a full day's sample; in addition, UFC tends to have significant variability as it may be affected by the volume of fluid intake by the patient during the day and may be affected by the presence or amount of impairment of kidney function (Rosmalen et al., Psychoneuroendocrinology 47:10 (2014)). Alternatively, plasma cortisol (a measure of the cortisol levels at the time the blood sample is taken) is used for dexamethasone suppression testing (which tests patient response to rapid increases in glucocorticoid levels). In addition, cortisol level can also be measured in a serum sample according to methods known in the art. As noted above, Cushing's syndrome is characterized by high levels of cortisol. Putignano et al. found no correlation between urinary free cortisol levels and either mean plasma cortisol or mean salivary cortisol levels; and that although salivary cortisol correlated with plasma cortisol levels in a population of 290 women with a wide range of cortisol levels, that correlation was lost for plasma cortisol concentrations greater than 500 nanomoles per liter (nmol/l) (Putignano et al., Eur. J. Endocrinol 145: 165-171 (2001)). In addition, Fleseriu et al. state that "[b]ecause mifepristone does not decrease cortisol production, measurement of this hormone should not be performed during treatment", and Torpy et al. state that "[t]here was no correlation between ACTH level and hypokalemia" (Ann. N.Y. Acad. Sci 970: 134-144 (2002).

The HPA axis is involved in maintaining proper potassium levels; thus, Cushing's syndrome, which is characterized by dysregulation of the HPA axis, includes the risk of developing hypokalemia. Cushing's syndrome patients at risk of developing hypokalemia include endogenous Cushing's syndrome patients, such as, e.g., ACTH-dependent Cushing's syndrome patients. In a study of Cushing's syndrome patients (including both ACTH-dependent and ACTH-independent Cushing's syndrome) treated with mifepristone, 22 (of 43) patients had serum potassium levels less than 3.5 mEq/L, of whom 3 had serum potassium levels less than 2.5 mEq/L (severe hypokalemia) (Fleseriu et al., 2012). Thus, significant numbers of Cushing's syndrome patients treated with mifepristone are at risk for developing hypokalemia. As noted above, hypokalemia can lead to increased risk of cardiac arrhythmias and other cardiac, muscular, and nervous system disorders. Cushing's patients may be at increased risk of cardiac arrhythmias, high blood pressure, and atherosclerosis; hypokalemia could further increase these risks, and could increase the risk of other disorders caused by, or associated with, hypokalemia.

Accordingly, methods for the identification of Cushing's syndrome patients who may be at high risk of developing hypokalemia are desired. Similarly, methods for reducing the risk of, or preventing, the development of hypokalemia in Cushing's syndrome patients at high risk of developing hypokalemia are desired. Methods for reducing the risk of, or preventing, the development of hypokalemia in ACTH-dependent Cushing's syndrome patients at high risk of developing hypokalemia are desired.

SUMMARY

Cushing's syndrome patients are at risk of developing hypokalemia, a serious and potentially life-threatening disorder. For example, Cushing's syndrome patients being administered a glucocorticoid receptor modulator (GRM), such as Cushing's syndrome patients receiving glucocorticoid receptor antagonist (GRA) treatment, e.g., receiving mifepristone treatment, are at risk of developing hypokalemia. Applicant discloses herein that such Cushing's syndrome patients may be particularly at risk of developing hypokalemia after initiating GRM treatment, or after an increase in their GRM dose; thus, Cushing's syndrome patients receiving mifepristone treatment may be particularly at risk of developing hypokalemia after initiating mifepristone treatment, or after an increase in their mifepristone dose.

Applicant discloses herein methods for identifying patients at risk for developing hypokalemia before their potassium levels drop below the normal range; that is, these methods are directed to Cushing's syndrome patients with normal potassium levels. These methods thus may prevent the development of, or may reduce the severity of, or duration of, hypokalemia. The methods disclosed herein provide improved methods for identifying and for monitoring patients at risk for developing hypokalemia. The methods disclosed herein provide improved methods for preventing the development of hypokalemia in Cushing's syndrome patients, including methods for preventing the development of hypokalemia in Cushing's syndrome patients treated with a GRM such as mifepristone. Thus, in embodiments, the present methods are directed to identifying GRM-treated (e.g., mifepristone-treated) Cushing's syndrome patients at risk for developing hypokalemia; for monitoring such patients at risk for developing hypokalemia; for prophylactically treating such patients at risk for developing hypokalemia; for preventing hypokalemia in such patients; and for reducing the duration or severity of hypokalemia in such patients.

While prior publications may describe certain relationships between ACTH and cortisol and hypokalemia, there is no report prior to this invention that establishes a direct correlation between serum ACTH or cortisol level and the likelihood of developing hypokalemia at a later time among Cushing's syndrome patients undergoing or about to undergo GRM treatment. For example, a 2012 publication by Auchus et al. (The Endocrine Society's 94th Annual Meeting and Expo, Jun. 23-26, 2012, Houston Tex.) indicates that higher 24-hour urinary free cortisol (UFC) levels (i.e., not plasma or serum concentrations of cortisol) in a patient prior to the start of mifepristone treatment tends to indicate a higher likelihood of the patient developing hypokalemia following mifepristone treatment. Measuring UFC has significant drawbacks as a diagnostic method: it takes 24-hours to complete the collection. Further, only a small and variable fraction of circulating cortisol is expelled in urine, which means UFC levels can vary widely depending on fluid intake, the efficiency of the patient's kidney function, and other factors, so that UFC is not a clear or reliable indicator of circulating cortisol. It is the circulating cortisol that is active and that may affect blood potassium levels, blood pressure, and other physiological variables, not urinary cortisol. Moreover, it is not clear whether, or how, mifepristone treatment may affect the fraction of circulating cortisol that is expelled in the urine. Thus, UFC measurements provide only an indirect, erratic, and unreliable indication of the active cortisol levels that may affect patient health, in contrast to measuring cortisol levels directly in the patient's plasma or serum samples (where the excess circulating cortisol that is causing the patient's disease is active), which can be completed in less than an hour, is more sensitive, and not affected by kidney function.

Similarly, although it is well known in the field of Cushing's syndrome research that biologically active forms of ACTH can cause the body to produce cortisol and so lead to increased cortisol levels and, in some cases, hypokalemia, it is also well known that the tumors, of both ectopic and pituitary origins, that cause Cushing's syndrome secrete an unpredictable, but sometimes significant, portion of ACTH that is biologically inert, which leads to a level of dissociation between the amount and activity of ACTH in Cushing's syndrome patients. Furthermore, ACTH-producing tumors in Cushing's syndrome patients vary significantly in size and in their efficiency of ACTH secretion in general and in response to cortisol. Thus, it was not believed before this invention that one could use ACTH or cortisol level in a Cushing's syndrome patient as a reliable indicator of the risk of future development of hypokalemia. This view is expressed in publications such as the 2002 Torpy et al. publication (Ann. N. Y. Acad. Sci. 970:134-144): "There was no relation between ACTH level and hypokalemia" (see abstract on page 135).

Accordingly, the present inventor has made surprising discoveries that, under specific circumstances, ACTH and cortisol levels can serve as reliable indicators of a Cushing's syndrome patient's risk of developing hypokalemia and discloses herein methods for identifying Cushing's syndrome patients who may be at risk for developing hypokalemia. For example, Applicant discloses herein methods for identifying Cushing's syndrome patients receiving mifepristone treatment who may be at increased risk for developing hypokalemia. Applicant discloses herein methods for prophylactically treating for hypokalemia such Cushing's syndrome patients identified as being at risk for developing hypokalemia. Applicant discloses herein methods for prophylactically treating for hypokalemia such Cushing's syndrome patients who may be at risk for developing hypokalemia. Applicant discloses herein methods for preventing the development of, or reducing the severity of, hypokalemia in Cushing's syndrome patients identified as being at risk for developing hypokalemia. Applicant discloses herein methods for preventing the development of, or reducing the severity of, hypokalemia in Cushing's syndrome patients who may be at risk for developing hypokalemia.

Mifepristone may be administered (e.g., once daily) to a subject suffering from Cushing's syndrome, such as ACTH-dependent Cushing's syndrome. In embodiments, ACTH-dependent Cushing's syndrome patients receiving mifepristone are at risk of developing hypokalemia, particularly after an increase in their mifepristone dose. In any or all of the methods disclosed herein, Cushing's syndrome patients include patients suffering from ACTH-dependent Cushing's; the Cushing's syndrome patient may be an adult suffering from endogenous Cushing's syndrome; may suffer from hyperglycemia secondary to hypercortisolism; may not be a candidate for surgery for Cushing's syndrome; may have failed surgery for Cushing's syndrome (i.e., Cushing's syndrome and/or its symptoms may persist following surgery for Cushing's syndrome); and combinations thereof. In embodiments, the patient is not otherwise in need of GRM treatment; e.g., the patient is not otherwise in need of mifepristone treatment.

Methods for treating a subject suffering from Cushing's syndrome, such as, e.g., ACTH-dependent Cushing's syndrome and at risk for hypokalemia resulting from GRM administration (e.g., following initiation of GRM treatment or following an increase in GRM dose during continued GRM treatment) are presented. In embodiments, methods for controlling hyperglycemia secondary to hypercortisolism in a Cushing's syndrome patient are disclosed. In embodiments, methods for reducing the risk of development of hypokalemia in such a patient are disclosed. In embodiments, methods for treating an adult patient with endogenous Cushing's syndrome having type 2 diabetes mellitus or glucose intolerance to control hyperglycemia secondary to hypercortisolism and of reducing the risk of development of hypokalemia in said patient are disclosed. In embodiments, such a patient has failed surgery, or is not a candidate for surgery, for Cushing's syndrome.

Applicant has determined that increased risk of developing hypokalemia in ACTH-dependent Cushing's patients with normal blood potassium levels may be identified by determining whether or not blood ACTH levels rise excessively following initial administration of a GRM or following an increased dose of GRM during continued GRM treatment. Blood ACTH levels may be determined, for example, by measurements of serum obtained from a patient in the morning (morning serum ACTH). Similarly, ACTH can also be measured in a plasma sample taken from a patient according to methods known in the art. In addition, Applicant discloses that increased risk of developing hypokalemia in Cushing's syndrome patients, such as, e.g., ACTH-dependent Cushing's patients with normal blood potassium levels may be identified by determining whether or not cortisol levels are high prior to initiation of GRM treatment for Cushing's syndrome (e.g., for hyperglycemia secondary to hypercortisolism in a Cushing's syndrome patient). Cortisol levels may be determined, e.g., by measuring cortisol in blood (e.g., serum or plasma), urine, or saliva. In embodiments, cortisol levels may be measured in serum samples obtained in the morning (morning serum cortisol). Plasma samples may be used in a similar fashion to assess cortisol level in a subject.

Applicant further discloses methods for preventing hypokalemia in a patient suffering from ACTH-dependent Cushing's syndrome, the methods comprising administering treatment for hypokalemia in a patient with normal potassium level if the ratio of the level of ACTH following GRM administration compared to the baseline level of ACTH (determined prior to GRM administration) is greater than a threshold level. The methods further comprise administering treatment for hypokalemia in a patient with normal potassium level if the ratio of the level of cortisol following GRM administration compared to the baseline level of cortisol (determined prior to GRM administration) is greater than a threshold level. The methods further comprise administering treatment for hypokalemia in a patient with normal potassium level if the ratio of the level of cortisol following GRM administration compared to the ACTH level following GRM administration) is greater than a threshold level.

For example, in embodiments, a threshold level for cortisol above which indicates risk of developing hypokalemia is about 700 nmol/L cortisol, or about 750 nmol/L cortisol, or about 800 nmol/L cortisol (which is also expressed as about 25 micrograms per deciliter, about 27 micrograms per deciliter, or about 29 micrograms per deciliter of cortisol, respectively), where cortisol is measured in serum samples taken in the morning. In preferred embodiments, such cortisol measurements are obtained from subjects who have not yet begun receiving glucocorticoid receptor modulator (GRM) treatment for Cushing's syndrome; e.g., prior to beginning mifepristone treatment for Cushing's syndrome. In embodiments of the methods disclosed herein, Cushing's patients who have not yet begun receiving mifepristone treatment and whose morning serum cortisol is at or above threshold (e.g., at or above 750 nmol/L) are administered prophylactic treatment for hypokalemia (e.g., are administered a mineralocorticoid receptor antagonist such as, e.g., spironolactone, or are administered supplemental potassium, or both). In further embodiments, cortisol is measured in saliva, or in urine (e.g., urinary free cortisol, such as 24-hour urinary cortisol). In embodiments, the threshold level for salivary cortisol is about 34 nmol/L. For example, in further embodiments of the methods disclosed herein, Cushing's patients who have not yet begun receiving mifepristone treatment and whose morning salivary cortisol is at or above threshold (e.g., at or above 34 nmol/L) are administered prophylactic treatment for hypokalemia (e.g., are administered a mineralocorticoid receptor antagonist such as, e.g., spironolactone, or are administered supplemental potassium, or both).

For example, in embodiments, a threshold level for ACTH above which indicates risk of developing hypokalemia is about 110 pg/mL, or about 112 pg/mL ACTH, or about 115 pg/mL, where ACTH is measured in serum samples taken in the morning. In preferred embodiments, such ACTH measurements are obtained from subjects who have been receiving glucocorticoid receptor modulator (GRM) treatment for Cushing's syndrome; e.g., from subjects treated with mifepristone for two weeks prior to measurement of morning serum ACTH. In embodiments of the methods disclosed herein, Cushing's patients who have been receiving mifepristone treatment for two weeks and whose morning serum ACTH is at or above threshold (e.g., at or above 120 pg/mL) are administered prophylactic treatment for hypokalemia (e.g., are administered a mineralocorticoid receptor antagonist such as, e.g., spironolactone, or are administered supplemental potassium, or both).

In Cushing's syndrome patients determined to have excessive ACTH, or excessive cortisol, or both, Applicant further discloses that administration of potassium, potassium sparing diuretics (e.g., spironolactone), or other hypokalemia treatment before symptoms of hypokalemia appear may reduce the risk of development of hypokalemia in those patients. In embodiments, administration of a hypokalemia treatment before symptoms of hypokalemia appear may prevent the development of, or reduce the severity of, hypokalemia in a Cushing's syndrome patient (e.g., an ACTH-dependent Cushing's syndrome patient, such as an adult patient suffering from hyperglycemia secondary to hypercortisolism due to endogenous Cushing's syndrome, and including an adult patient suffering from hyperglycemia secondary to hypercortisolism due to endogenous Cushing's syndrome and having type 2 diabetes or glucose intolerance) otherwise at risk of developing hypokalemia following an increase in GRM dose. In embodiments, the GRM is mifepristone.

Applicant has determined that the risk of developing hypokalemia in Cushing's syndrome patients, such as ACTH-dependent Cushing's patients, with normal blood potassium levels may be identified by determining whether or not morning serum ACTH levels are excessive following GRM treatment (e.g., following initiation of GRM treatment or following an increase in GRM dose during continued GRM treatment). In embodiments, the GRM is mifepristone, and excessive ACTH rise is determined if the morning serum ACTH level is at or above about 110 pg/mL, e.g., at or above 112 pg/mL, following mifepristone treatment for a time, such as for two weeks, at a mifepristone dose (e.g., 300 mg mifepristone per day, or 600 mg mifepristone per day, or 900 mg mifepristone per day, or 1200 mg mifepristone per day). In embodiments, Cushing's syndrome patients, such as ACTH-dependent Cushing's patients, with normal blood potassium levels, are at risk of developing hypokalemia if their blood ACTH levels are above about 112 pg/mL following an increase in GRM dose. In embodiments, the GRM is mifepristone, and excessive ACTH rise is determined if the ACTH level in blood rises above about 112 pg/mL following an increase in GRM dose (e.g., administration of a once-daily dose of 600 mg mifepristone after the patient has been receiving 300 mg mifepristone once daily, or administration of a once-daily dose of 900 mg mifepristone after the patient has been receiving 600 mg mifepristone once daily, or administration of a once-daily dose of 1200 mg mifepristone after the patient has been receiving 900 mg mifepristone once daily). The methods disclosed herein allow the identification of patients at risk for developing hypokalemia, e.g., during treatment for Cushing's syndrome or related conditions, without the need to directly monitor the patient's potassium levels. However, in some cases, the methods further comprise measuring a potassium level of the patient, e.g., in the blood of a patient (such as in a morning serum sample obtained from the patient).

Accordingly, Applicant discloses methods for determining, prior to initiating GRM treatment, whether or not a patient suffering from Cushing's syndrome (e.g., ACTH-dependent Cushing's syndrome) is at risk for developing hypokalemia. In embodiments, the patient has morning serum cortisol levels at or above about 700 nmol/L prior to beginning GRM treatment for Cushing's syndrome. In embodiments, the morning serum cortisol level is at or above 750 nmol/L prior to beginning GRM treatment for Cushing's syndrome. In embodiments, the GRM is mifepristone. In embodiments, the mifepristone dose for the treatment of Cushing's syndrome is 300 mg mifepristone; or 600 mg mifepristone; or 900 mg mifepristone; or 1200 mg mifepristone. In embodiments, the mifepristone dose is a once-daily dose. In embodiments, the patient has normal blood potassium levels prior to an increase in mifepristone dose.

Accordingly, Applicant discloses methods for determining whether or not a patient suffering from Cushing's syndrome (e.g., ACTH-dependent Cushing's syndrome) is at risk for developing hypokalemia due to GRM treatment (e.g., following initiation of GRM treatment or following an increase in GRM dose during continued GRM treatment). In embodiments, the patient has morning serum ACTH levels at or above about 100 pg/mL ACTH following GRM treatment for a time. In embodiments, the morning serum ACTH level is at or above 112 pg/mL ACTH following GRM treatment for a time. In embodiments, the GRM is mifepristone. In embodiments, the mifepristone dose comprises an increase in the mifepristone dose to a dose of 600 mg mifepristone after the patient has been receiving 300 mg mifepristone per day; or to a dose of 900 mg mifepristone after the patient has been receiving 600 mg mifepristone per day; or to a once-daily dose of 1200 mg mifepristone after the patient has been receiving 900 mg mifepristone per day. In embodiments, the mifepristone dose is a once-daily dose. In embodiments, the patient has normal blood potassium levels prior to an increase in mifepristone dose.

The methods disclosed herein allow the identification of patients at risk for developing hypokalemia, e.g., during treatment for Cushing's syndrome or related conditions, and provide methods for prophylactically treating the patient for hypokalemia effective to reduce the risk of devloping hypokalemia, or effective to reduce the severity of hypokalemia in the patient, or to reduce the duration of hypokalemia in the patient. The present methods provide such identification, and such prophylactic treatments, without the need to directly monitor the patient's potassium levels (although potassium levels may be monitored if desired). The present methods avoid the potentially dangerous practice of prophylactically pre-treating every patient for the risk of hypokalemia; such treatment in a patient not at risk for hypokalemia could lead to serious consequences (e.g., development of hyperkalemia, a potentially life-threatening condition, or adrenal insufficiency, or other serious condition). Accordingly, the present methods provide the advantage of reducing the risk of developing a serious medical condition (hypokalemia) in patient identified as being at high risk for that condition, while avoiding unnecessary and potentially dangerous treatment of patients who are not at high risk for that condition.

In one particular aspect, the present invention provides a novel method for therapeutic or prophylactic treatment of a patient who may develop or is at a heightened risk of later developing hypokalemia, due to the patient having been given or being scheduled to receive treatment for Cushing's syndrome or related conditions by administration of a GRM. The method includes the step of administering to the patient an effective amount of a therapeutic agent for the condition of hypokalemia, the patient being defined as a patient (especially an adult patient) with endogenous Cushing's syndrome having type 2 diabetes mellitus or glucose intolerance to control hyperglycemia secondary to hypercortisolism, (1) who has received or is scheduled to receive treatment by administration of a GRM, such as mifepristone; and (2) whose ACTH or cortisol level (e.g., serum or plasma level), after at least having GRM administration once or prior to receiving any GRM administration, respectively, has been measured and shown to elevate above a pre-determined threshold for ACTH or cortisol level. More specifically, the measurement of cortisol level prior to the start or initiation of GRM treatment is particularly useful for treating/preventing the early onset type of hypokalemia: for example, if a patient who is scheduled to receive GRM administration has been detected to have a morning serum level of at least or above about 750 nmol/L (or about 27 µg/dl) cortisol before the GRM administration, the patient is deemed at heighten risk of developing hypokalemia after the initiation of GRM administration (e.g., within the first two weeks of the start of GRM administration) and is therefore given an effective amount of a therapeutic agent for the condition of hypokalemia concurrently with the GRM administration as it is initiated. On the other hand, the measurement of ACTH after the start of GRM administration (e.g., a week or two weeks after the initial GRM administration started and has been ongoing) and before a dose escalation of GRM is particularly useful for treating/preventing the late onset type of hypokalemia: for example, if a patient has been given GRM treatment for about two weeks and is about to receive an increased dose of GRM (dose escalation), and the patient has been detected to have a morning serum level of ACTH of at least or above about 112 pg/ml, the patient is deemed at heighten risk of developing hypokalemia after the dose escalation of GRM administration and is therefore given an effective amount of a therapeutic agent for the condition of hypokalemia prior to or concurrently with the increased dose of GRM administration. In some cases, the patient being given hypokalemia medication to reduce the risk of or to prevent development of the late onset type of hypokalemia has been previously tested and found to have no increased risk for the early onset type of hypokalemia and thus has not been prophylactically treated for the early onset type of hypokalemia. Typically, the patients receiving prophylactic treatment for hypokalemia do not have lower than normal blood potassium level prior to the start of the prophylactic treatment.

In some embodiments of this invention, the GRM is mifepristone (also known as RU-486, RU486, RU38.486) the chemical name of which is: 11-β-(4-dimethylaminophenyl)-17β-hydroxy-17α-(1-propynyl)-estra-4,9-dien-3-one), also written as 17-beta-hydroxy-11-beta-(4-dimethylaminophenyl)-17-alpha-(1-propynyl)-estra-4,9-dien-3-one). In some embodiments, the patient's ACTH level is measured in a blood sample (especially a plasma or serum sample), a saliva sample, or a urine sample. In some embodiments, the patient's cortisol level is measured in a blood sample (especially a plasma or serum sample), a saliva sample, or a urine sample. The sample used in measuring cortisol level may be taken from the patient before the first dose of GRM administration. The sample used in measuring ACTH level may be taken from the patient after at least one dose of GRM administration: for example, after a first daily dose of GRM administration (e.g., mifepristone administration) at 300 mg/day, 600 mg/day, or 900 mg/day, a sample is taken before the second dose is given to the patient, e.g., within 1, 2, 3, 4, 5, 6, 7, 8, 9, 10 days or up to 2 weeks after the first GRM administration, but before a second, typically higher, daily dose of GRM (e.g., mifeprisone) administration, for example, after 600 mg/day, 900 mg/day, or 1200 mg/day of mifepristone having been administered. In some embodiments, the first dose at about 300 mg/day of a GRM such as mifepristone is administered to a patient; after about 7-21 days, for example, about 2 weeks, of administration at this first dose, the patient is set to enter a second phase of treatment and to receive a second and higher dose of GRM (such as mifepristone) at about 600 mg/day, it is at this conjuncture that the patient's risk of developing hypokalemia is assessed based on the patient's ACTH level and the patient is treated as appropriate in accordance with the methods described herein.

Due to the nature of ACTH or cortisol presence in a patient's tissue sample and bodily fluids, the determination of a potential increase in ACTH or cortisol level typically requires samples of the same type (e.g., serum samples) and samples taken from the patients and standard control subjects at about the same time during the day (e.g., in the morning at about 6 AM, 8 AM, 10 AM, or in the afternoon at about 12 PM, 2 PM, 4 PM, or 6 PM of the day).

In some embodiments, the post-GRM administration level of ACTH is measured to be at least about 100% higher than a standard control or average normal value (or at least twice the standard control or average normal value), i.e., the ACTH level found in samples of the same type taken from normal subjects. In some embodiments, the post-GRM administration level of ACTH is measured to be at least about 80, 100, 108, 110, 112, 115, or 120 pg/ml or higher in a plasma or serum sample taken from the patient in the morning (e.g., between about 6 AM to about 10 AM, for example, at about 7, 8, or 9 AM). In some embodiments, the patient's cortisol level has been measured prior to the start of GRM administration, and the pre-GRM administration level of cortisol is measured to be at least about 100% higher than a standard control or average normal value (or at least twice the standard control or average normal value), i.e., the cortisol level found in samples of the same type taken from normal subjects. In some embodiments, the pre-GRM administration level of cortisol is measured to be at least about 700, 750, or 800 nmol/L (about 25, 27, or 29 µg/dl, respectively) or higher in a plasma or serum sample taken from the patient in the morning (e.g., between about 6 AM to about 10 AM, for example, at about 7, 8, or 9 AM).

In some embodiments, the patient suitable for receiving the treatment method of this application is an adult who may be of either gender and who is in his/her 20s, 30s, 40s, 50s, 60s, 70s, 80s or older, for example, between the ages of about 20-30, 30-40, 40-50, 50-60, 60-70, 70-80, or 80 or 85 and above. In some embodiments, the patient is one who is without any symptoms of hypokalemia and is not otherwise in need of treatment by any medication for hypokalemia.

The methods disclosed herein provide the surprising advantages of reduced risk of, reduced occurrence, and prevention, of hypokalemia in Cushing's syndrome patients treated with mifepristone. Further advantages include the use of plasma levels of ACTH and cortisol as indicators, which are quicker and more consistent measures of patient status than, for example, urinary free cortisol (which requires 24 hour urine collection). On the other hand, the methods disclosed herein also allow physicians to identify those among Cushing's syndrome patients who do not have elevated risk of developing hypokalemia upon beginning to receive GRM administration or upon receiving an increased dose of GRM administration, and who therefore do not need to be given any prophylactic treatment for hypokalemia such that any unnecessary side-effects of such prophylactic treatment, which can be life-threatening, can be avoided.

The methods disclosed herein provide the advantages of reduced risk of, reduced duration and severity of, delayed onset of, and/or complete prevention of, hypokalemia and hypokalemia-associated symptoms, including reducing the risk or, or prevention of, arrhythmias, sudden cardiac arrest, and other life-threatening symptoms associated with hypokalemia. Further symptoms associated with hypokalemia which may be prevented, or reduced by the present methods include, e.g., fatigue; edema; hypertension; muscle weakness, cramps, or muscle spasms; neurological problems including paresthesia and paralysis; renal problems such as polyuria, polydipsia, and nocturia; gastrointestinal disorders including abdominal cramps, constipation, nausea, and vomiting; long Q-T syndrome; cardiac palpitations and arrhythmias. They also help physicians avoid unnecessary prophylactic treatment for hypokalemia, which can cause serious adverse events. These advantages surprisingly improve patient outcomes, avoid serious risks associated with mifepristone treatment for Cushing's syndrome, and provide treating physicians with new and improved tools for management of mifepristone treatment of Cushing's syndrome.

In summary, the present invention provide new methods for assessing the risk or likelihood of developing hypokalemia at a later time in a patient, especially an adult patient with endogenous Cushing's syndrome having type 2 diabetes mellitus or glucose intolerance to control hyperglycemia secondary to hypercortisolism who has received or is scheduled to receive treatment by administration of a glucocorticoid receptor modulator (GRM) (such as mifepristone), based on (1) detecting an above-threshold level of serum or plasma ACTH found in a blood sample taken from the patient after the initial GRM administration (for example, 1 or 2 weeks after the initial and continuous GRM administration at a lower dosage) but before subsequent GRM administration of an increased dosage; or (2) detecting an above-threshold level of serum or plasma cortisol found in a blood sample taken from the patient prior to the start of GRM administration. Upon identifying a patient who has a heightened risk of later developing hypokalemia even though who has not yet manifested any symptom of the condition, the present invention further provides novel methods for prophylactically treating the patient by administration of one or more therapeutically active agents for the condition in an effective amount to delay onset of hypokalemia, or reduce severity/duration of hypokalemia, or completely prevent occurrence of hypokalemia: in the case of (1), the patient receives an effective amount of a therapeutic agent for hypokalemia concurrently started or co-administered with the increased dose of a GRM, and may continue to receive the therapeutic agent continuously along with the higher dose of GRM. In the case of (2), the patient receives an effective amount of a therapeutic agent for hypokalemia concurrently started or co-administered with the initial dose of a GRM, and may continue to receive the therapeutic agent continuously along with the GRM administration.

For instance, to identify patients at high risk of developing hypokalemia following GRM initiation, measure morning serum cortisol prior to starting GRM treatment. If serum cortisol is above about 27 µg/dL, prophylactic therapy (e.g., with mineralocorticoid antagonists) should be initiated concurrently with GRM administration. To identify patients at high risk of developing hypokalemia following an increase in the dose of GRM treatment, about two weeks after starting GRM treatment (e.g., at about 7 to about 21 days, such as about 14 days), measure morning ACTH levels. If ACTH levels are above about 112 pg/mL, prophylactic treatment for hypokalemia (e.g., with mineralocorticoid antagonists) should be initiated or intensified before the dose of GRM is increased.

The present methods provide the advantages of a) reducing the risk of developing, and preventing, hypokalemia in Cushing's syndrome patients receiving GRM treatment, by prophylactic administration of hypokalemia treatment before the patient's potassium drops below normal levels, avoiding the serious and potentially life-threatening symptoms of hypokalemia; and b) by identifying those patients at high risk, avoiding unnecessary administration of hypokalemia treatments to patients who are not at high risk of hypokalemia, thus avoiding the risk of (iatrogenic) hyperkalemia, which has its own serious side effects.

BRIEF DESCRIPTION OF THE DRAWINGS

FIG. 1 shows the association between ACTH levels and potassium (<3.5 mmol/L, ≥3.5 mmol/L). It shows that patients with potassium levels<3.5 mmol/L had on average higher ACTH levels on the same study day.

DETAILED DESCRIPTION

A. Introduction

Figure 1:
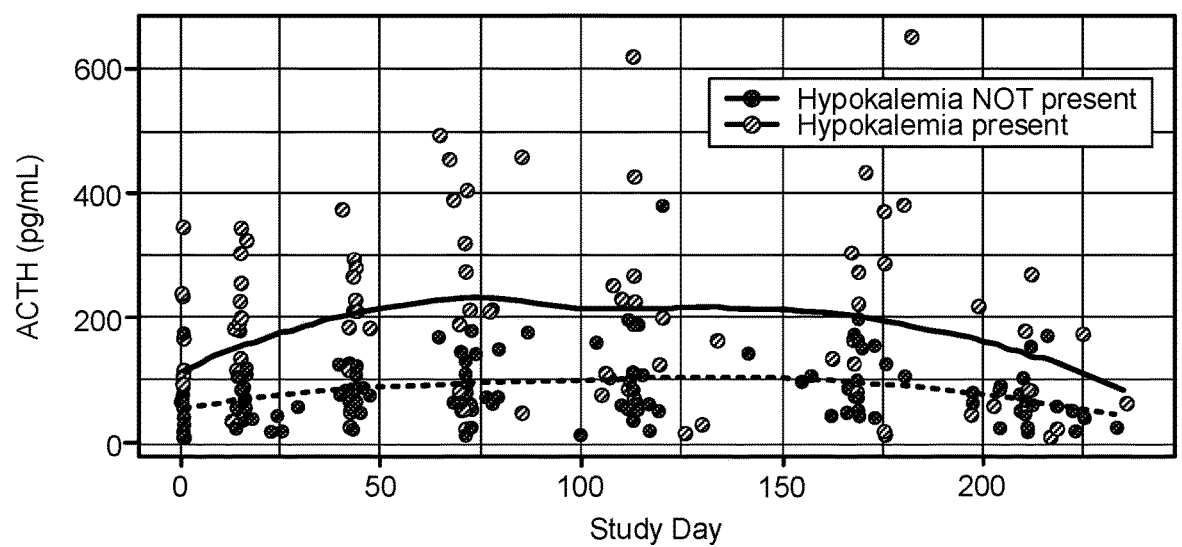
FIG. 1 shows plasma ACTH (pg/mL) over the course of study (study days 0 to 210) for two groups of Cushing's patients who received mifepristone at doses of 300 mg/day (days 0 to 13); 600 mg/day (days 14 to 41); 900 mg/day (days 42 to 69); and 1200 mg/day (days 70 onward). The first group (lower line) had blood potassium levels that remained within the normal range. The second group (upper line) experienced low potassium levels (less than or equal to 3.5 mEq/L): their blood potassium levels were below the normal range. Note that the hypokalemic patients had plasma ACTH levels that exceeded 100 pg/mL when the mifepristone dose was increased by 300 mg/day; i.e., from 300 mg/day to 600 mg/day, and which remained above that level for the duration of the study. In contrast, those Cushing's patients who did not experience hypokalemia had plasma ACTH levels which remained near 100 pg/mL, and did not show dramatic rises in ACTH levels when the mifepristone dose was raised by 300 mg/day (the plasma ACTH level of these patients did not show abrupt increases when the mifepristone dose was raised from 300 mg/day to 600 mg/day; nor when it was raised from 600 mg/day to 900 g/day; nor when it was raised from 900 mg/day to 1200 g/day).

Cushing's syndrome patients treated with a glucocorticoid receptor modulator (GRM) such as mifepristone may be at risk for developing hypokalemia. Hypokalemia was observed in 44% of Cushing's syndrome patients receiving mifepristone treatment. As disclosed herein, GRM-treated Cushing's syndrome patients that are at high risk of developing hypokalemia following GRM treatment initiation may be identified by measuring morning serum cortisol prior to initiation of the GRM treatment. A morning serum cortisol level at or above a threshold level is indicative of high risk of developing hypokalemia during GRM treatment for Cushing's syndrome. In embodiments, the threshold morning cortisol level measured prior to initiating GRM treatment that is indicative of high risk of developing hypokalemia during GRM treatment for Cushing's syndrome is a morning serum cortisol level that is at or above about 1.5 times normal morning serum cortisol levels; or that is at or above about 2 times, or about 2.5 times, or about 3 times, normal morning serum cortisol levels (where normal morning serum cortisol levels are determined by mean levels measured in samples obtained from multiple normal subjects). In embodiments, a morning serum cortisol level at or above a threshold level of 750 nmol/L is indicative of high risk of developing hypokalemia during GRM treatment for Cushing's syndrome. Patients whose morning serum cortisol level is at or above the threshold level (e.g., at or above 750 nmol/L or at or above about 2 times normal morning serum cortisol levels) prior to initiating GRM treatment should be given prophylactic treatment for hypokalemia concurrently with the GRM administration. Such prophylactic treatment may include administration of mineralocorticoid antagonists or other potassium-sparing diuretic; may include potassium supplementation (e.g., oral, intravenous, or other), or both.

Accordingly, Applicant discloses herein novel methods of reducing the risk of hypokalemia in Cushing's syndrome patients treated with a glucocorticoid receptor modulator (GRM), reducing the severity of hypokalemia in Cushing's syndrome patients treated with a GRM, of preventing hypokalemia in Cushing's syndrome patients treated with a GRM, of identifying Cushing's syndrome patients at high risk of developing hypokalemia when being treated with a GRM, and other treatment and identifying methods. The GR may be, e.g., mifepristone. Applicant has discovered that there are strong associations between the development of hypokalemia and 1) serum cortisol levels at baseline (prior to treatment with mifepristone), and 2) ACTH levels after 2 weeks of mifepristone administration. For example, early onset hypokalemia (appearing within the first 2 weeks of mifepristone treatment of Cushing's syndrome patients) is most correlated with high baseline serum cortisol levels (>750 nmol/L). For further example, late onset hypokalemia (appearing at or after 2 weeks of mifepristone treatment of Cushing's syndrome patients) has the strongest correlation with high ACTH levels (≥112 pg/mL) after 2 weeks of treatment with mifepristone. A yet further example is that severe and/or recurrent hypokalemia has strong correlation with high ACTH levels (≥112 pg/mL). (A patient suffers from hypokalemia if their serum potassium level is less than 3.5 milliequivalents per liter (mEq/L). A patient suffers from severe hypokalemia if their serum potassium level is less than or equal to 2.5 mEq/L. A patient suffers from recurrent hypokalemia if they suffer two or more instances of hypokalemia, whether severe or not.)

As disclosed herein, GRM-treated Cushing's syndrome patients that are at high risk of developing hypokalemia during GRM treatment may be identified by measuring morning serum ACTH after starting the GRM treatment (e.g., measured two weeks after starting the GRM treatment). A morning serum ACTH level at or above a threshold level is indicative of high risk of developing hypokalemia during GRM treatment for Cushing's syndrome. In embodiments, the threshold morning ACTH level measured after starting GRM treatment that is indicative of high risk of developing hypokalemia during GRM treatment for Cushing's syndrome is a morning serum ACTH level that is at or above about 1.5 times normal morning serum ACTH levels; or that is at or above about 2 times, or about 2.5 times, or about 3 times, normal morning serum ACTH levels (where normal morning serum ACTH levels are determined by mean levels measured in samples obtained from multiple normal subjects). In embodiments, the threshold morning ACTH level indicative of developing hypokalemia may be 1.5 time, or 2 times, or 2.5 times, or 3 times, the baseline morning serum ACTH level (where baseline morning serum ACTH level is determined from at least one morning serum ACTH measurement from a sample obtained from the patient prior to beginning GRM administration, or prior to increasing the GRM dose). In embodiments, the threshold morning ACTH level measured after starting GRM treatment that is indicative of high risk of developing hypokalemia during GRM treatment for Cushing's syndrome is a morning serum ACTH level that is at or above 112 pg/mL. In embodiments, a morning serum ACTH level at or above the threshold level (e.g., at or above about 2 times normal (or baseline) morning serum ACTH levels, or at or above 112 pg/mL) measured two weeks after initiation of GRM treatment is indicative of high risk of developing hypokalemia during GRM treatment for Cushing's syndrome. Patients whose morning ACTH levels are at or above the threshold level when measured at a time after initiation of GRM treatment should be given prophylactic treatment for hypokalemia. In embodiments, patients whose morning ACTH levels are at or above the threshold level when measured two weeks after initiation of GRM treatment should be given prophylactic treatment for hypokalemia. Such prophylactic treatment may include administration of mineralocorticoid antagonists or other potassium-sparing diuretic; may include potassium supplementation (e.g., oral, intravenous, or other), or both.

In embodiments, such prophylactic treatment for hypokalemia may be administered prior to GRM dose escalation where morning ACTH levels are at or above threshold (e.g., twice normal, or twice baseline, or 112 pg/mL). For example, the morning ACTH levels of a patient receiving 300 mg per day GRM may be measured, and if found to be at or above threshold, the patient may be administered prophylactic treatment for hypokalemia when the daily dose of GRM is increased to 600 mg/day. For further example, the morning ACTH levels of a patient receiving 600 mg per day GRM may be measured, and if found to be at or above threshold, the patient may be administered prophylactic treatment for hypokalemia when the daily dose of GRM is increased to 900 mg/day. For yet further example, the morning ACTH levels of a patient receiving 900 mg per day GRM may be measured, and if found to be at or above threshold, the patient may be administered prophylactic treatment for hypokalemia when the daily dose of GRM is increased to 1200 mg/day. In embodiments, the GRM may be, e.g., mifepristone.

Accordingly, Applicant discloses methods for identifying patients at risk for, and for prophylactically treating, hypokalemia in mifepristone-treated Cushing's syndrome patients. The methods disclosed herein can be used to treat a Cushing's syndrome patient; in embodiments, the Cushing's syndrome patient suffers from ACTH-dependent Cushing's syndrome and is at risk for hypokalemia resulting from increased GRM dose. In embodiments, the patient is an adult having endogenous Cushing's syndrome and suffering from hyperglycemia secondary to hypercortisolism. In embodiments, the patient is an adult having type 2 diabetes or glucose intolerance, having endogenous Cushing's syndrome and suffering from hyperglycemia secondary to hypercortisolism. In embodiments, the patient may have failed surgery for Cushing's syndrome, or may not be a candidate for surgery for Cushing's syndrome. In embodiments, the methods are suitable for controlling hyperglycemia secondary to hypercortisolism in an adult patient suffering from endogenous Cushing's syndrome and who has failed surgery for Cushing's syndrome, or is not a candidate for surgery for Cushing's syndrome. In embodiments, the methods are suitable for controlling hyperglycemia secondary to hypercortisolism in an adult with patient type 2 diabetes or glucose intolerance and suffering from endogenous Cushing's syndrome, who has failed surgery for Cushing's syndrome, or is not a candidate for surgery for Cushing's syndrome.

Applicant discloses herein the surprising discovery that increased risk of developing hypokalemia in ACTH-dependent Cushing's patients may be identified by determining whether or not ACTH levels, or cortisol levels, or both, rise excessively following an increase in GRM dose. Administration of potassium, spironolactone, or other hypokalemia treatment before symptoms of hypokalemia appear in the patient, based on such determination of excessive rise in ACTH or cortisol, may reduce the risk of development of hypokalemia in those patients, and may prevent the development of, or reduce the severity of, hypokalemia in a Cushing's syndrome patient (e.g., an ACTH-dependent Cushing's syndrome patient) otherwise at risk of developing hypokalemia following an increase in GRM dose. In embodiments, the GRM is mifepristone.

As disclosed above, in embodiments, the threshold morning ACTH level indicative of increased risk of developing hypokalemia may be 112 pg/mL. In embodiments, the risk of developing hypokalemia in such patients may be identified by determining whether or not morning serum ACTH levels rise above a threshold level of about 100 pg/mL (e.g., 112 pg/ml) following initiation of mifepristone treatment or following an increase in GRM dose, where the GRM may be mifepristone; e.g., determining whether or not morning serum ACTH levels rise above about 100 pg/mL (e.g., 112 pg/ml) following initiation of mifepristone treatment or following an increase in mifepristone dose. In embodiments, the increase in mifepristone dose is following initiation of mifepristone treatment, or is an increase from a once-daily dose of 300 mg mifepristone per day to a once-daily dose of 600 mg mifepristone; or from a once-daily dose of 600 mg mifepristone to 900 mg mifepristone once daily; or from a once-daily dose of 900 mg mifepristone to 1200 mg mifepristone once daily. In embodiments, the threshold morning serum ACTH level is 112 pg/mL. In embodiments, the threshold morning serum ACTH level is about 100 pg/ml, or about 105 pg/ml, or about 110 pg/mL, or about 115 pg/mL, or about 120 pg/mL.

As disclosed above, in embodiments, the threshold morning ACTH level indicative of increased risk of developing hypokalemia may be 1.5 times, or 2 times, or 2.5 times, or 3 times the normal morning serum ACTH level (where normal morning serum ACTH levels are determined by mean levels measured in samples obtained from multiple normal subjects). In embodiments, the threshold morning ACTH level indicative of developing hypokalemia may be 1.5 time, or 2 times, or 2.5 times, or 3 times, the baseline morning serum ACTH level (where baseline morning serum ACTH level is determined from at least one morning serum ACTH measurement from a sample obtained from the patient prior to beginning GRM administration, or prior to increasing the GRM dose). In embodiments, the risk of developing hypokalemia in such patients may be identified by determining whether or not morning serum ACTH levels rise above a threshold level of about 1.5 times, or 2 times, or 2.5 times, or 3 times the normal (or baseline) morning serum ACTH level following an increase in GRM dose, where the GRM may be mifepristone; e.g., determining whether or not morning serum ACTH levels rise above about 1.5 times, or 2 times, or 2.5 times, or 3 times the normal morning serum ACTH level following initiation of mifepristone treatment or following an increase in mifepristone dose. In embodiments, the increase in mifepristone dose is from a once-daily dose of 300 mg mifepristone per day to a once-daily dose of 600 mg mifepristone; or from a once-daily dose of 600 mg mifepristone to 900 mg mifepristone once daily; or from a once-daily dose of 900 mg mifepristone to 1200 mg mifepristone once daily.

In further embodiments, the risk of developing hypokalemia in such patients may be identified by determining whether or not cortisol levels are above a threshold level prior to initiation of GRM treatment, or rise above a threshold level following an increase in GRM dose; e.g., determining whether or not cortisol levels are above a threshold level prior to initiation of mifepristone treatment, or rise above a threshold level following an increase in mifepristone dose, where the cortisol levels may be measured from blood samples, urine samples, saliva samples, or combinations thereof. In embodiments, the increase in mifepristone dose is from a once-daily dose of 300 mg mifepristone per day to a once-daily dose of 600 mg mifepristone; or from a once-daily dose of 600 mg mifepristone to 900 mg mifepristone once daily; or from a once-daily dose of 900 mg mifepristone to 1200 mg mifepristone once daily. In embodiments, the threshold level is a morning serum cortisol level of about 700 nmol/L (25 µg/dL), or about 750 nmol/L (27 µg/dL), or about 800 nmol/L (29 µg/dL). In embodiments, the threshold morning cortisol level indicative of increased risk of developing hypokalemia may be 1.5 times, or 2 times, or 2.5 times, or 3 times the normal morning serum cortisol level (where normal morning serum cortisol levels are determined by mean levels measured in samples obtained from multiple normal subjects). In embodiments, the threshold morning cortisol level indicative of developing hypokalemia may be 1.5 time, or 2 times, or 2.5 times, or 3 times, the baseline morning serum cortisol level (where baseline morning serum cortisol level is determined from at least one morning serum cortisol measurement from a sample obtained from the patient prior to beginning GRM administration, or prior to increasing the GRM dose).

Applicant has determined that increased risk of developing hypokalemia in ACTH-dependent Cushing's patients with normal blood potassium levels may be identified by determining whether or not blood ACTH levels rise excessively following administration of an initial or an increased GRM dose. In Cushing's syndrome patients determined to have high levels of ACTH following initiation of GRM treatment, or following an increase in GRM dose; or determined to have high cortisol prior to administration of GRM, or both, Applicant further discloses that administration of potassium, spironolactone, or other hypokalemia treatment before symptoms of hypokalemia appear may reduce the risk of development of hypokalemia in those patients. In embodiments, administration of potassium, or spironolactone, or other hypokalemia treatment before symptoms of hypokalemia appear may prevent the development of, or reduce the severity of, hypokalemia in a Cushing's syndrome patient (e.g., an ACTH-dependent Cushing's syndrome patient) otherwise at risk of developing hypokalemia following an increase in GRM dose. In embodiments, the GRM is mifepristone.

Applicant has determined that the risk of developing hypokalemia in Cushing's syndrome patients, such as ACTH-dependent Cushing's patients, with normal blood potassium levels may be identified by determining whether or not blood ACTH levels rise excessively following an increase in GRM dose. In embodiments, the GRM is mifepristone, and excessive ACTH rise is determined if the ACTH level in blood rises above about 100 pg/mL (e.g., 112 pg/mL) following an increase in mifepristone dose (e.g., administration of a once-daily dose of 600 mg mifepristone after the patient has been receiving 300 mg mifepristone once daily, or administration of a once-daily dose of 900 mg mifepristone after the patient has been receiving 600 mg mifepristone once daily). In embodiments, Cushing's syndrome patients, such as ACTH-dependent Cushing's patients, with normal blood potassium levels, are at risk of developing hypokalemia if their blood ACTH levels are at or above about 112 pg/mL following two weeks of GRM treatment at an initial or at an increased GRM dose. In embodiments, the GRM is mifepristone, and excessive ACTH rise is determined if the ACTH level in blood rises above about 100 pg/mL (e.g., 112 pg/mL) following an increase in GRM dose (e.g., administration of a once-daily dose of 300 mg mifepristone for two weeks to a patient who has not previously received mifepristone, or administration of a once-daily dose of 600 mg mifepristone after the patient has been receiving 300 mg mifepristone once daily, or administration of a once-daily dose of 900 mg mifepristone after the patient has been receiving 600 mg mifepristone once daily). The methods disclosed herein allow the identification of patients at risk for developing hypokalemia, e.g., during treatment for Cushing's syndrome or related conditions, without the need to directly monitor the patient's potassium levels. However, in some cases, the methods further comprise measuring a potassium level of the patient, e.g., in the blood of a patient (such as in a blood sample obtained from the patient).

Accordingly, Applicant discloses methods for determining whether or not a patient suffering from Cushing's syndrome (e.g., ACTH-dependent Cushing's syndrome) is at risk for developing hypokalemia following an increase in the patient's GRM dose. In embodiments, the patient has morning serum ACTH levels at or above about 100 pg/mL ACTH following an increase in the GRM dose. In embodiments, the morning serum ACTH level is at or above about 112 pg/mL ACTH. In embodiments, the morning serum ACTH level is at or above about 112 pg/mL ACTH following two weeks of GRM treatment, or is at or above about 112 pg/mL ACTH following an increase in the GRM dose. In embodiments, the GRM is mifepristone. In embodiments, an increase in the mifepristone dose is a once-daily dose of 600 mg mifepristone after the patient has been receiving 300 mg mifepristone once daily; or a once-daily dose of 900 mg mifepristone after the patient has been receiving 600 mg mifepristone once daily; or a once-daily dose of 1200 mg mifepristone after the patient has been receiving 900 mg mifepristone once daily. In embodiments, the patient has normal blood potassium levels prior to an increase in GRM dose.

B. Definitions

The following definitions are presented to aid in the understanding of the disclosure herein, and are not meant to be limiting.

A mineralocorticoid receptor (MR), also known as a type I glucocorticoid receptor (GR I), is activated by aldosterone in humans.

The term "glucocorticosteroid" ("GC") or "glucocorticoid" refers to a steroid hormone that binds to a glucocorticoid receptor. Glucocorticosteroids are typically characterized by having 21 carbon atoms, an α,β-unsaturated ketone in ring A, and an α-ketol group attached to ring D. They differ in the extent of oxygenation or hydroxylation at C-11, C-17, and C-19; see Rawn, "Biosynthesis and Transport of Membrane Lipids and Formation of Cholesterol Derivatives," in Biochemistry, Daisy et al. (eds.), 1989, pg. 567.

The term "cortisol" refers to the naturally occurring glucocorticoid hormone (also known as hydrocortisone) having the structure:

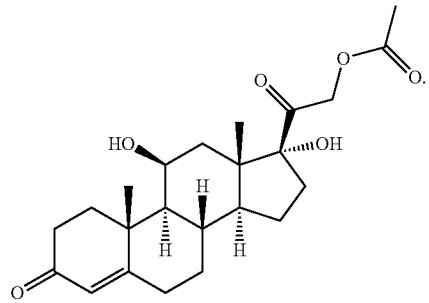

Cortisol is typically produced by the zona fasciculata of the adrenal gland.

As used herein, the term glucocorticoid receptor (GR) refers to an intracellular receptor that binds glucocorticoids, such as cortisol, dexamethasone, or other molecules. A glucocorticoid receptor, also known as a corticosteroid receptor or as a type II glucocorticoid receptor (GR II), and in humans, as a cortisol receptor, is activated by cortisol in humans (or, e.g., by corticosterone ("cortisone") in some other animals, such as rats and mice). The human cortisol receptor (GR II receptor, Genbank: P04150) specifically binds to cortisol and/or cortisol analogs (e.g. dexamethasone). The term includes isoforms of GR II, recombinant GRII, and mutated GRIT.

As used herein, the term glucocorticoid receptor modulator (GRM) refers to an agent that affects the action of a glucocorticoid receptor (GR). Such modulation may include activation (agonist action), partial activation (partial agonist action), inhibition (reduction in activation of the receptor under conditions where it would otherwise be activated, such as in the presence of cortisol), and blockade (complete or near complete suppression of activation of the receptor under conditions where it would otherwise be activated, such as in the presence of cortisol). GRMs may affect the activity of a GR by increasing or by decreasing the activity of the GR. GRMs include steroids, including mifepristone, and, in embodiments, include pyrimidinediones; azadecalins; fused-ring azadecalins; heteroaryl-ketone fused-ring azadecalins; and other compounds.

As used herein, the term "selective glucocorticoid receptor modulator" (SGRM) refers to any composition or compound which inhibits any biological response associated with the binding of a GR to an agonist. By "selective," the drug preferentially binds to the GR rather than other intracellular receptors, such as the progesterone receptor (PR), the mineralocorticoid receptor (MR) or the androgen receptor (AR).

As used herein, the terms "glucocorticoid agonist", "glucocorticoid receptor agonist", "glucocorticoid receptor type II agonist", and "GRIT agonist" refer to a compound or agent which may bind to and activate a cortisol receptor. Such agents include, for example, cortisol, dexamethosone, prednisone, and other compounds and agents which bind to and activate a GRII.

As used herein, the terms "glucocorticoid antagonist", "glucocorticoid receptor antagonist", "glucocorticoid antagonist", "glucocorticoid receptor type II antagonist", "GRII antagonist", and "GRA" refer to agents that inhibit the action of a cortisol receptor; such inhibition may include interfering with the binding of a glucocorticoid agonist such as cortisol, dexamethosone, or other compound or agent which may bind to and activate a cortisol receptor. A GRA is a glucocorticoid receptor modulator. Inhibition constants ($K_i$) for GRAs against the human cortisol receptor may be between about 0.0001 nM and about 1,000 nM; preferably may be between about 0.0005 nM and about 10 nM, and most preferably between about 0.001 nM and about 1 nM.

The terms "glucocorticoid receptor antagonist," "GRA," and "glucocorticoid receptor blocker" refer to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist," "SGRA," and "specific glucocorticoid receptor blocker" refer to any composition or compound which inhibits any biological response associated with the binding of a GR to an agonist. By "specific," we intend the drug to preferentially bind to the GR rather than another nuclear receptors, such as mineralocorticoid receptor (MR) or progesterone receptor (PR).

As used herein, GRM, SGRM, and GRA compounds may be identified by binding assays and functional assays (e.g., cell-based assays) known to those of skill in the art. Preferred binding assays suitable for use in identifying and characterizing GRM, SGRM, and GRA compounds are disclosed, for example, in U.S. Pat. No. 7,928,237 (e.g., Section III, under the heading "Binding Assays"; and under the heading "Cell-Based Assays"); in U.S. Pat. No. 8,685, 973 (e.g., Section VI, under heading A: "Binding Assays" and under heading B, "Cell-Based Assays"); in U.S. Pat. No. 8,859,774 (e.g., Section VII, under heading A: "Binding Assays"; and under heading B, "Cell-Based Assays"); and in U.S. Pat. No. 10,047,082 (e.g., Section V, under heading A: "Binding Assays"; and under heading B, "Cell-Based Assays"). The contents of U.S. Pat. Nos. 7,928,237; 8,685, 973; 8,859,774; and 10,047,082 are hereby incorporated by reference herein in their entireties. In some embodiments, administration of a GRM, such as mifepristone, may lead to increase in cortisol level in a patient.

Mifepristone is a GRM which binds to GRII (and which also binds to a progesterone receptor). As used herein, the term "mifepristone" refers to 11β-(4-dimethylaminophenyl)-17β-hydroxy-17α-(1-propynyl)-estra-4,9-dien-3-one), also referred to as RU486, or as RU38.486, or as 17-beta-hydroxy-11-beta-(4-dimethyl-aminophenyl)-17-alpha-(1-propynyl)-estra-4,9-dien-3-one). Mifepristone binds to GR, typically with high affinity, and inhibits the biological effects initiated/mediated by the binding of any cortisol or cortisol analogue to a GR receptor (and thus is a GRM that is a GRA). Salts, hydrates and prodrugs of mifepristone are all included in the term "mifepristone" as used herein. Thus, used herein, "mifepristone" refers to the molecule that has the following structure:

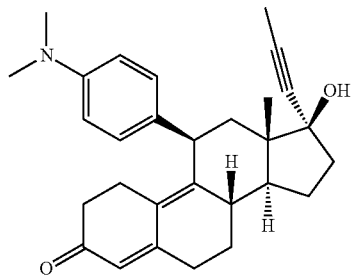

and to salts, hydrates and prodrugs thereof, and pharmaceutical compositions thereof. Mifepristone is also sometimes abbreviated as "mife" and "MIFE".

Metabolites of mifepristone include RU42633 (desmethylmifepristone: (8 S,11R,13 S,14S,17S)-17-hydroxy-13-methyl-11-[4-(methylamino)phenyl]-17-prop-1-ynyl-1,2,6, 7,8,11,12,14,15,16-decahydrocyclopenta[a]phenanthren-3-one); RU42698 (22-hydroxy mifepristone: (8 S,11R,13S, 14S,17S)-11-[4-(dimethylamino)phenyl]-17-hydroxy-17-(3-hydroxyprop-1-ynyl)-13-methyl-1,2,6,7,8,11,12,14,15, 16-decahydrocyclopenta[a]phenanthren-3-one); and RU42848 (didesmethylmifepristone: (8S,11R,13S,14S, 17S)-11-(4-aminophenyl)-17-hydroxy-13-methyl-17-prop-1-ynyl-1,2,6,7,8,11,12,14,15,16-decahydrocyclopenta[a] phenanthren-3-one), among others.

In some embodiments, the GRM comprises a steroidal backbone with at least one phenyl-containing moiety in the 11-β position of the steroidal backbone. In some cases, the phenyl-containing moiety in the 11-β position of the steroidal backbone is a dimethylaminophenyl moiety. In some cases, the GRM is mifepristone. In some embodiments, the GRM is selected from the group consisting of 11β-(4-dimethylaminoethoxyphenyl)-17α-propynyl-17β-hydroxy-4,9 estradien-3-one and (17α)-17-hydroxy-19-(4-methylphenyl)androsta-4,9(11)-dien-3-one. In some embodiments, the GRM is (11β,17β)-11-(1,3-benzodioxol-5-yl)-17-hydroxy-17-(1-propynyl)estra-4,9-dien-3-one.

The term "steroidal backbone" in the context of glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

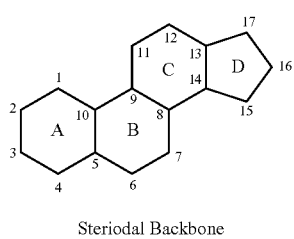

Formula I

Steriodal Backbone

The two most commonly known classes of structural modifications of the cortisol steroid backbone to create glucocorticoid antagonists include modifications of the 11-β hydroxy group and modification of the 17-β side chain (See, e. g., Lefebvre (1989) J. Steroid Biochem. 33: 557-563).

As used herein, the phrase "non-steroidal backbone" in the context of glucocorticoid receptor antagonists containing such refers to glucocorticoid receptor antagonists that do not share structural homology to, or are not modifications of, cortisol. Such compounds include, for example, small molecules, synthetic mimetics and analogs of proteins, including partially peptidic, pseudopeptidic and non-peptidic molecular entities.

In some embodiments, the GRM is a non-steroidal compound. In embodiments, non-steroidal GRM compounds include compounds having a cyclohexyl-pyrimidine backbone; non-steroidal GRM compounds having a fused azadecalin backbone; non-steroidal GRM compounds having a heteroaryl ketone fused azadecalin backbone; and non-steroidal GRM compounds having an octahydro fused azadecalin backbone. Exemplary glucocorticoid receptor antagonists having a cyclohexyl-pyrimidine backbone include those described in U.S. Pat. No. 8,685,973. Exemplary glucocorticoid receptor antagonists having a fused azadecalin backbone include those described in U.S. Pat. Nos. 7,928,237; and 8,461,172. Exemplary glucocorticoid receptor antagonists having a heteroaryl ketone fused azadecalin backbone include those described in U.S. Pat. No. 8,859,774. Exemplary glucocorticoid receptor antagonists having an octohydro fused azadecalin backbone include those described in U.S. Patent Application Publication 20150148341.

"Patient", "patient in need", "subject", "subject in need" and the like refer to a person having, or suspected of having, a disease or condition which may be treated by administration of a therapeutic drug.

As used herein, the term "Cushing's syndrome" refers to an array of symptoms caused by excess cortisol. Cushing's syndrome includes endogenous Cushing's syndrome and ectopic Cushing's syndrome. Such symptoms include, for example, elevated blood pressure, elevated blood glucose, increased weight (typically in the mid-section, and in the face causing a characteristic "moon-face"), immune suppression, thin skin, acne, depression, hirsutism, and other symptoms.

The terms "Cushing Disease" and "Cushing's Disease" refer to pituitary-dependent Cushing's syndrome, e.g., excess cortisol caused by pituitary abnormality (typically a pituitary tumor), e.g., conditions in which the pituitary gland releases too much ACTH as a result of a tumor located in or near the pituitary gland, or as a result of excess growth (hyperplasia) of the pituitary gland. Cushing Disease is a form of Cushing's syndrome. The term Cushing's syndrome thus includes reference to Cushing's Disease.

The term "endogenous Cushing's syndrome" refers to a form of Cushing's syndrome, where the excess cortisol level is caused by the body's own overproduction of cortisol. Patients having endogenous Cushing's syndrome include adult patients also having type 2 diabetes; include adult patients also suffering from glucose intolerance; include adult patients having hyperglycemia secondary to hypercortisolism; include adult patients having hyperglycemia secondary to hypercortisolism who have type 2 diabetes or glucose intolerance; include adult patients who have failed surgery for Cushing's syndrome; include adult patients who are not candidates for surgery for Cushing's syndrome; and patients having any or all of these symptoms and conditions.

As used herein, a "patient suffering from Cushing's syndrome" refers to any patient suffering from Cushing's syndrome, including endogenous Cushing's syndrome; Cushing's Disease; or a condition associated with Cushing's syndrome. A condition associated with Cushing's syndrome may be, without limitation, a condition associated with endogenous Cushing's syndrome; hyperglycemia secondary to hypercortisolism; a condition of hypercortisolism in an endogenous Cushing's syndrome patient, said patient having type 2 diabetes mellitus or glucose intolerance; a condition of hyperglycemia secondary to hypercortisolism in an endogenous Cushing's syndrome patient, said patient having type 2 diabetes mellitus or glucose intolerance and having failed surgery; hyperglycemia secondary to hypercortisolism in an endogenous Cushing's syndrome patient, said patient having type 2 diabetes mellitus or glucose intolerance and having failed surgery or who is not a candidate for surgery; and other conditions associated with Cushing's syndrome.

Treating Cushing's syndrome, including endogenous Cushing's syndrome and Cushing's disease, may include administration of a glucocorticoid receptor modulator (GRM), such as, e.g., mifepristone. Treating Cushing's syndrome, including endogenous Cushing's syndrome, may include controlling hyperglycemia secondary to hypercortisolism. Treating Cushing's syndrome, including endogenous Cushing's syndrome, may include controlling hyperglycemia secondary to hypercortisolism in an adult with patient type 2 diabetes or glucose intolerance and suffering from endogenous Cushing's syndrome, who has failed surgery for Cushing's syndrome, or is not a candidate for surgery for Cushing's syndrome.

As used herein, the terms "monitor", "to monitor", "monitoring" and the like refer to a physician or other person paying attention to, keeping track of, following the measurements of or course of, one or more of analyte measurements (e.g., potassium levels, cortisol levels, ACTH levels, or other measurements), patient symptoms, patient response to treatment, and other clinical signs related to a disease or disorder, the symptoms of a disease or disorder, the course of a disease or disorder, and the course of treatment of a disease or disorder. Monitoring may include scheduling an appointment for a patient to see a physician or other practitioner, or to have a test (e.g., a blood, urine, or saliva test) performed, as well as inspecting or evaluating the results of such an appointment or test.

As used herein, the term "Adrenocorticotrophic Hormone" (ACTH) refers to the peptide hormone produced by the anterior pituitary gland. ACTH stimulates secretion of cortisol and other glucocorticoids (GCs) by specialized cells of the adrenal cortex, which help cells synthesize glucose, catabolize proteins, mobilize free fatty acids and inhibit inflammation in allergic responses. In healthy mammals, ACTH secretion is tightly regulated. ACTH secretion is positively regulated by corticotropin releasing hormone (CRH), which is released by the hypothalamus. ACTH secretion is negatively regulated by cortisol and other glucocorticoids.

The term "Adrenocorticotropic hormone (ACTH)-dependent Cushing's syndrome" refers to a form of endogenous Cushing's syndrome, which is caused by abnormal production of ACTH. There are two major forms of ACTH-dependent Cushing's syndrome: Cushing Disease (accounting for about 80% of the cases) and ectopic ACTH syndrome (accounting for 20% of the cases).

"Treat", "treating" and "treatment" refer to any indicia of success in the treatment or amelioration of a pathology or condition, including any objective or subjective parameter such as abatement; remission; diminishing of symptoms or making the pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters; including the results of a physical examination; histopathological examination (e.g., analysis of biopsied tissue); laboratory analysis of urine, saliva, tissue samples, serum, plasma, or blood; or imaging.

As used herein, "treating a patient who is suffering from Cushing's syndrome", or treating a subject who is suffering from Cushing's syndrome", or similar phrases refer to, without limitation, treating a patient suffering from Cushing's syndrome, including endogenous Cushing's syndrome; treating a patient suffering from Cushing's Disease; or treating a patient suffering from a condition associated with Cushing's syndrome. A condition associated with Cushing's syndrome is discussed above. For example, treating a patient who is suffering from Cushing's syndrome may include administering mifepristone or other GRM to control hyperglycemia secondary to hypercortisolism in adult patients with endogenous Cushing's syndrome who have type 2 diabetes mellitus or glucose intolerance and have failed surgery or are not candidates for surgery.

As used herein, the terms "administer," "administering," "administered," "administration," and the like, refer to providing a compound or a composition (e.g., one described herein), to a subject or patient. Thus, for example, "administration to a patient" refers to the delivery of a drug or other therapeutic into the body of a patient in need of treatment by the drug or therapeutic, effective to achieve a therapeutic effect. Administration may be by any suitable route of administration, including, for example, oral administration; intravenous administration; subcutaneous administration; parenteral administration; intra-arterial administration; nasal administration; topical administration; and other routes of administration.

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, epicutaneous, subcutaneous, intraperitoneal, intraventricular, and intracranial. Other modes of delivery include, but are not limited to, the use of liposomal formulations, intravenous infusion, and transdermal patches.

The term "sample" refers to a biological sample obtained from a human subject. The sample can be any cell, tissue or fluid from a human subject, for example, a sample of blood (including whole blood or any fraction of thereof, e.g., plasma or serum), saliva, urine, tear, sweat, and the like. Samples can be subject to various treatment, storage or processing procedures before being analyzed according to the methods described herein. Generally, the terms "sample" or "samples" are not intended to be limited by their source, origin, manner of procurement, treatment, processing, storage or analysis, or any modification.

The term "morning serum sample" refers to a serum sample obtained from a human subject in the morning, where morning may be a time between about 6 AM to about 10 AM, or between about 7 AM and about 9 AM, or other time understood as during the morning.

The term "morning serum cortisol sample" refers to a morning serum sample in which the level, e.g., the concentration, of cortisol is measured.

The term "morning serum ACTH sample" refers to a morning serum sample in which the level, e.g., the concentration, of ACTH is measured.

As used herein, the term "AUC" means the area under the plasma or serum concentration-time curve, and serves as a measure of the plasma levels of a drug in a subject to whom the drug has been administered.

As used herein, the term "$C_{max}$" means the maximum observed plasma or serum concentration of a drug in a subject to whom the drug has been administered.

The term "measuring the level," in the context of cortisol, ACTH, mifepristone, or other compounds, refers to determining, detecting, or quantitating the amount, level, or concentration of, for example, cortisol, ACTH, mifepristone, or other compound in a sample obtained from a subject. Plasma or serum samples are often used for measuring ACTH or cortisol level. In preferred embodiments of this invention, a serum or plasma sample taken from a patient in the morning (e.g., between about 6 AM to about 10 AM, for example, at about 6, 7, 8, or 9 AM) is used for measuring the level of ACTH by a radioimmunoassay (RIA), most preferable a two-site RIA, such as performed by Quest Diagnostics (Secaucus, N.J. 07094). In other preferred embodiments, a serum or plasma sample taken from a patient in the morning (e.g., between about 6 AM to about 10 AM, for example, at about 6, 7, 8, or 9 AM) is used for measuring the level of cortisol by high-performance liquid chromatography/triple quadrupole-mass spectrometry (LC-MS/MS), such as performed by Quest Diagnostics (Secaucus, N.J. 07094).

The term "elevated level", "elevated amount", or "elevated concentration" refers to the level or amount of the analyte that is higher than the normal reference value for that analyte.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art. The effective amount can be an amount effective to reduce cortisol binding to GR, or to reduce cortisol activation of GR, in a patient.

As used herein, the term "compound" is used to denote a molecular moiety of unique, identifiable chemical structure. A molecular moiety ("compound") may exist in a free species form, in which it is not associated with other molecules. A compound may also exist as part of a larger aggregate, in which it is associated with other molecule(s), but nevertheless retains its chemical identity. A solvate, in which the molecular moiety of defined chemical structure ("compound") is associated with a molecule(s) of a solvent, is an example of such an associated form. A hydrate is a solvate in which the associated solvent is water. The recitation of a "compound" refers to the molecular moiety itself (of the recited structure), regardless of whether it exists in a free form or an associated form.

Potassium levels in blood of normal adult humans typically range from about 3.5 milliEquivalents per Liter (mEq/L) to about 5.5 or 6 mEq/L. Levels outside this range can lead to serious clinical abnormalities, including, for example, changes in blood pressure, heart rate, muscle and nerve activity, kidney and fluid problems, and other clinical abnormalities. Plasma or serum samples are often used for measuring potassium level in a patient's blood.

Hypokalemia is the condition of low potassium levels in the blood. As noted above, normal levels of potassium are between about 3.5 mEq/L and about 5.3 mEq/L. Potassium levels below about 3.5 mEq/L are typically considered to be low, and to indicate hypokalemia, and to require observation and medical care; levels below about 2.5 mEq/L are considered severe hypokalemia, and may require immediate clinical attention. Such low potassium levels (below about 3.5 mEq/L) can be serious, leading to, for example, neuromuscular disorders including cramps, paresthesia, paralysis, and other disorders; renal and urinary disorders; cardiovascular disorders including hypertension, heart palpitations, irregular heart rate; and other clinical abnormalities. Hypokalemia can lead to increased risk of sudden cardiac arrest. Thus, hypokalemia is a serious condition, and can be life-threatening. Treatment for hypokalemia may include oral or intravenous potassium (e.g., a potassium salt such as KCl); administration of a potassium-sparing diuretic such as, e.g., triamterene, amiloride, or other such drug; administration of a mineralocorticoid receptor antagonist such as spironolactone, eplerenone, or other such drug; administration of a steroid synthesis inhibitor such as, e.g., ketoconazole or itraconazole; or other treatment.

Somatostatin and somatostatin analogs (e.g., octreotide, pasireotide, and lanreotide) may be used to treat hypokalemia. Somatostatin and somatostatin analogs are believed to act to treat hypokalemia, at least in part, by reducing ACTH levels, thus leading to reduced cortisol levels, and so to reduced mineralocorticoid activation.

Steroid synthesis inhibitor include, for example, ketoconazole, itraconazole, fluconazole, metyrapone, etomidate, and other drugs, and may be used to treat hypokalemia. Steroid synthesis inhibitors are believed to act, at least in part, by reducing cortisol synthesis, thus leading to reduced cortisol levels, and so to reduced mineralocorticoid activation.

Potassium-sparing diuretics such as, e.g., amiloride (MIDAMOR®) and triamterene (e.g., DYRENIUM®) may be used to treat hypokalemia.

Mineralocorticoid receptor antagonists (also termed mineralocorticoid antagonists, or antimineralocorticoids) reduce or block the activation of MR. Mineralocorticoid antagonists include, for example, spironolactone (e.g., ALDACTONE®), eplenerone (INSPRA®), canrenone, and fineronone. Mineralocorticoid antagonists may be administered to treat hypokalemia. For example, spironolactone (e.g., from about 50 mg per day up to about 300 mg per day) may be administered to control hypokalemia.

One method of treating hypokalemia includes potassium replacement therapy (potassium supplementation) by oral administration of potassium (typically 40-120 mEq per day, although in some cases about 10 mEq/day up to about 340 mEQ/day may be administered). Alternatively, or in addition, potassium replacement therapy (potassium supplementation) may be performed by intravenous administration of potassium.

As used herein, the term "composition" is intended to encompass a product comprising the specified ingredients such as the said compounds, their tautomeric forms, their derivatives, their analogues, their stereoisomers, their polymorphs, their deuterated species, their pharmaceutically acceptable salts, esters, ethers, metabolites, mixtures of isomers, their pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing compounds of the present invention and their pharmaceutically acceptable carriers.

In some embodiments, the term "consisting essentially of" refers to a composition in a formulation whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" can refer to compositions which contain the active ingredient and components which facilitate the release of the active ingredient. For example, the composition can contain one or more components that provide extended release of the active ingredient over time to the subject. In some embodiments, the term "consisting" refers to a composition, which contains the active ingredient and a pharmaceutically acceptable carrier or excipient.

"Pharmaceutically-acceptable excipient" and "pharmaceutically-acceptable carrier" refer to a substance that aids the administration of an active agent to—and absorption by—a subject and can be included in the compositions of the present invention without causing a significant adverse toxicological effect on the patient. Non-limiting examples of pharmaceutically-acceptable excipients include water, NaCl, normal saline solutions, lactated Ringer's, normal sucrose, normal glucose, binders, fillers, disintegrants, lubricants, coatings, sweeteners, flavors and colors, and the like. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. One of ordinary skill in the art will recognize that other pharmaceutical excipients are useful in the present invention.

The term "normal level" refers to the average level of an analyte as determined by measurements of samples obtained from multiple normal subjects.

The term "normal cortisol level" refers to the average level of cortisol as determined by measurements of samples (e.g., serum samples) obtained from multiple normal subjects.

The term "normal level" refers to the average level of ACTH as determined by measurements of samples (e.g., serum samples) obtained from multiple normal subjects.

"Standard control" as used herein refers to a sample comprising a predetermined amount of an analyte (such as ACTH or cortisol) suitable for the use of an application of the present invention, in order to serve as a comparison basis for providing an indication of the relative amount of the analyte (e.g., ACTH or cortisol) that is present in a test sample. A sample serving as a standard control provides an average amount of an analyte such as ACTH or cortisol that is representative for a defined sample type (e.g., plasma, serum, saliva, or urine) taken at a defined time of the day (e.g., 8 AM) from an average individual who is not suffering from or at increased risk of later developing hypokalemia or any associated disorder or complication and has been given the same GRM treatment. As used herein, a "blood sample" may be a whole blood sample, serum sample, plasma sample, or blood cell sample as appropriate for measuring an analyte level by art-known methods according to conventional use. Similarly, "blood level" of a particular analyte maybe the level of the analyte in the whole blood, serum, plasma, or blood cells. For example, the blood level of potassium, ACTH, or cortisol maybe the level of each analyte in a serum or plasma sample taken from a subject being tested.

The term "average," as used in the context of describing an individual (especially a human subject) who does not have and is not at increased risk of developing hypokalemia or any related condition or disorder prior to receiving GRM treatment, refers to certain characteristics, such as the level or amount of an analyte (such as ACTH or cortisol) present in a sample taken from the individual without receiving GRM treatment, that are representative of the average amount or level of the analyte found in a randomly selected group of individual subjects who have not been diagnosed with and are not susceptible to hypokalemia or any related diseases or conditions and therefore can serve as an "average normal value" or "standard control value" for the particular analyte prior to GRM treatment. This selected group should comprise a sufficient number of individuals (e.g., at least 200 or 500 or more) such that the average value (i.e., level or amount) of the analyte of interest (e.g., ACTH or cortisol) assessed among these individuals reflects, with reasonable accuracy, the corresponding level or amount of the analyite found in the general population of non-hypokalemic individuals with no known risk for the disorder or related conditions upon receiving GRM treatment. In some cases, the selected group of individuals generally have the same gender, are similar in age (e.g., within a 5- or 10-year age difference from one another), have similar ethnic and medical backgrounds. Depending on the analyte, the average value or standard control value may need to be ascertained from samples taken from these individuals at about the same time during the day (e.g., 6 AM, 8 AM, 12 PM, 4 PM, or 6 PM). The average or standard control value of any particular analyte may also vary depending on the specific assay or assay format (including the specific reagents) utilized for quantitatively measuring the analyte, and therefore can be made available either by way of experimentation or by way of assay manufacturer's information.

The term "about" when used in reference to a pre-determined value denotes a range encompassing ±10% of the pre-determined value.

The term "steady state of plasma or serum GRM concentration" or the like, as used herein, describes a state in which the GRM level in the plasma or serum does not significantly increase (e.g., no more than about 10%, 15%, 20%, 25%, or 30% increase) with subsequent doses of GRM administration in a Cushing's syndrome patient who has been receiving a daily (or other regular frequency of administration) dose of a GRM (such as mifepristone) over a period of several days (e.g., at least about 3, 4, or 5 days, at least about 5 to about 10 days, or about 7 to about 21 days, such as about 14 days).

C. Hypokalemia Risk

The methods disclosed herein are applicable for identifying patients at high risk for developing hypokalemia before potassium levels in those patients drop below safe levels. Normal potassium levels are typically between about 3.5 mEq/L and about 5.3 mEq/L. Levels of potassium below 3.5 mEq/L are considered hypokalemic, and levels below about 2.5 mEq/L are severely hypokalemic. Hypokalemia can cause life-threatening cardiac problems including long QT syndrome, cardiac arrhythmias, and can lead to sudden death. Identifying patients who may become hypokalemic before their potassium levels drop below 3.5 mEq/L could avoid serious complications in those patients, since the effects of low potassium are immediate, and the condition can become life-threatening very quickly. Applicant discloses herein methods for identifying, and for providing prophylactic treatment to, patients at high risk for developing hypokalemia before potassium levels in those patients drop below safe levels, effective to prevent the development of, or reduce the severity of, hypokalemia in those patients.

Cushing's syndrome patients receiving GRM treatment, such as mifepristone treatment, are be at risk of developing hypokalemia. Identification of Cushing's syndrome patients who may on a course to develop hypokalemia before the potassium levels drop below normal, or before other symptoms arise, allows prophylactic treatment that can avoid the development of hypokalemia, rather than merely attempt to alleviate it after it has become evident.

Applicant has discovered that measurement of ACTH levels, cortisol levels, or both, of Cushing's syndrome patients receiving GRM treatment, such as mifepristone treatment, allows identification of those patients who would otherwise go on to suffer from hypokalemia, by determining, e.g., one or both of the following: cortisol levels above about 700 nmol/L (e.g., at or above 750 nmol/L) following a period of time (e.g., two weeks) after initiation of treatment with a GRM such as mifepristone; and ACTH levels above about 100 pg/mL (e.g., at or above 112 pg/mL) following a period of time (e.g., two weeks) after initiation of treatment with a GRM such as mifepristone.

The types of samples that are suitable for ACTH determination can be serum, plasma, saliva, urine, or any other biological fluid taken from a subject. In preferred embodiments, the sample is a serum sample, or is a plasma sample.

The level of ACTH can be measured using various methods, including but not limited to, immunoassays, e.g., competitive immunoassay, radioimmunoassay (MA), immunofluorometric enzyme assay, and ELISA; competitive protein-binding assays; liquid chromatography (e.g., HPLC); and mass spectrometry, e.g., high-performance liquid chromatography/triple quadrupole-mass spectrometry (LC-MS/MS). Commercial kits for measuring ACTH are readily available, e.g., from Mayo clinic (Test ID: ACTH), Siemens Healthcare Global (Immulite® 2000 ACTH assay), and Roche Molecular Diagnostics (Catalog No. 03255751190). In preferred embodiments, ACTH levels are measured using a radioimmunoassay (RIA), most preferable a two-site MA, such as performed by Quest Diagnostics (Secaucus, N.J. 07094).

The types of samples that are suitable for cortisol determination can be serum, plasma, saliva, urine, or any other biological fluid taken from a subject. In preferred embodiments, the sample is a serum sample, or is a plasma sample. The level of cortisol can be measured using various methods, including but not limited to, immunoassays, e.g., competitive immunoassay, radioimmunoassay (MA), immunofluorometric enzyme assay, and ELISA; competitive protein-binding assays; liquid chromatography (e.g., HPLC); and mass spectrometry, e.g., high-performance liquid chromatography/triple quadrupole-mass spectrometry (LC-MS/MS). In preferred embodiments, cortisol levels are measured using LC-MS/MS, such as performed by Quest Diagnostics (Secaucus, N.J. 07094).

D. Glucocorticoid Receptor Modulators (GRM)

Generally, treatment of Cushing's syndrome, such as ACTH-dependent Cushing's syndrome, can be provided by administering an effective amount of a glucocorticoid receptor modulator (GRM) of any chemical structure or mechanism of action. In embodiments, the GRM is mifepristone. In embodiments, the GRM is a selective GRM (SGRM). In embodiments, prevention of hypokalemia in Cushing's syndrome patients, or reducing the risk of hypokalemia in Cushing's syndrome patients, or identifying Cushing's syndrome patients at particular risk of developing hypokalemia, where such patients are receiving treatment comprising administration of a GRM, such as mifepristone, can be provided by administering a treatment for hypokalemia before hypokalemia is observed in the patient when ACTH, or cortisol, or both, are determined to rise excessively following increase in the GRM dosage administered to the Cushing's syndrome patient. In preferred embodiments, the GRM is mifepristone. Provided herein are further classes of exemplary GRMs, including exemplary nonsteroidal SGRMs, and specific members of such classes. However, one of skill in the art will readily recognize other related or unrelated GRMs and SGRMs that can be employed in the treatment methods described herein.

E. Treatment for Hypokalemia

Agents suitable for use in treating hypokalemia in combination with the GRM as disclosed herein include potassium supplements; potassium-sparing diuretics; mineralocorticoid receptor antagonists; steroid synthesis inhibitors (e.g., ketoconazole, itraconazole, and others); and other agents that either raise potassium or reduce cortisol levels (e.g., mitotane). Thus, treatment for hypokalemia, including prophylactic treatment for hypokalemia (that is, prior to the patient's potassium levels dropping below 3.5 mEq/L) includes, without limitation, administration of one or more of potassium supplements; potassium-sparing diuretics; mineralcorticoid receptor antagonists; steroid synthesis inhibitors; and other agents that either raise potassium or reduce cortisol levels. Typically, treatment for hypokalemia is prophylactic treatment when administered to a subject whose potassium levels are not below the lower limit for normal potassium (i.e., not below 3.5 mEq/L). However, in embodiments, hypokalemia treatments may be considered prophylactic treatment for hypokalemia when administered to patients with potassium levels minimally below about 3.5 mEq/L (e.g., at about 3.4, or 3.3 mEq/L).

In still further embodiments, more than one agent for treating hypokalemia may be administered simultaneously, or sequentially in any order during the entire or portions of the treatment period. The two agents may be administered following the same or different dosing regimens.

The present methods can be combined with other means of Cushing's syndrome treatment such as surgery, radiation, targeted therapy, immunotherapy, or other methods.

In embodiments, determination that the cortisol level in a patient's blood (e.g., the morning serum cortisol level) is above about 700 nmol/L (e.g., at or above 750 nmol/L) identifies that patient as one at risk of hypokalemia, and indicates that prophylactic hypokalemia treatment should be initiated.

In embodiments, determination that the ACTH level in a patient's blood (e.g., the morning serum ACTH level) is above about 100 pg/mL (e.g., at or above 112 pg/mL) identifies that patient as one at risk of hypokalemia, and indicates that prophylactic hypokalemia treatment should be initiated.

The GRM or SGRM therapy disclosed herein can reduce the risk of hypokalemia, and may prevent development of hypokalemia, and thus confer beneficial clinical outcome to Cushing's syndrome patients. The clinical benefits of preventive and prophylactic treatment of hypokalemia include reducing risk of fatigue, edema, and hypertension in the patient; avoiding or reducing the risk of muscle weakness, cramps, and muscle spasms; avoiding or reducing the risk of neurological problems such as paresthesia and paralysis; avoiding or reducing the risk of renal problems such as polyuria, polydipsia, and nocturia; avoiding or reducing the risk of gastrointestinal disorders such as abdominal cramps, constipation, nausea, and vomiting; avoiding or reducing the risk of long Q-T syndrome; avoiding or reducing the risk of cardiac palpitations and arrhythmias; avoiding or reducing risk of sudden cardiac arrest; and other benefits.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All patents, patent applications, patent publications, and other references cited herein, both supra and infra, are hereby incorporated by reference herein.

EXAMPLES

The following examples are presented by way of illustration of embodiments of the methods disclosed herein, and serve to illustrate, but not to limit, the present disclosure of methods of treating patients suffering from Cushing's syndrome, including Cushing's Disease.

Example 1

High Serum Cortisol Levels Prior to Mifepristone Administration and High Serum ACTH Levels Following Two Weeks of Mifepristone Treatment Predict Hypokalemia All events of severe/recurrent hypokalemia were preceded by declining of potassium levels: 3 of 4 patients had previous low potassium values and one patient had previously normal potassium levels that were declining prior to the development of the event.

FIG. 1 shows the association between ACTH levels and potassium (3.5 mmol/L, ≥3.5 mmol/L). It shows that patients with potassium levels<3.5 mmol/L had on average higher ACTH levels on the same study day.

Figure 2:
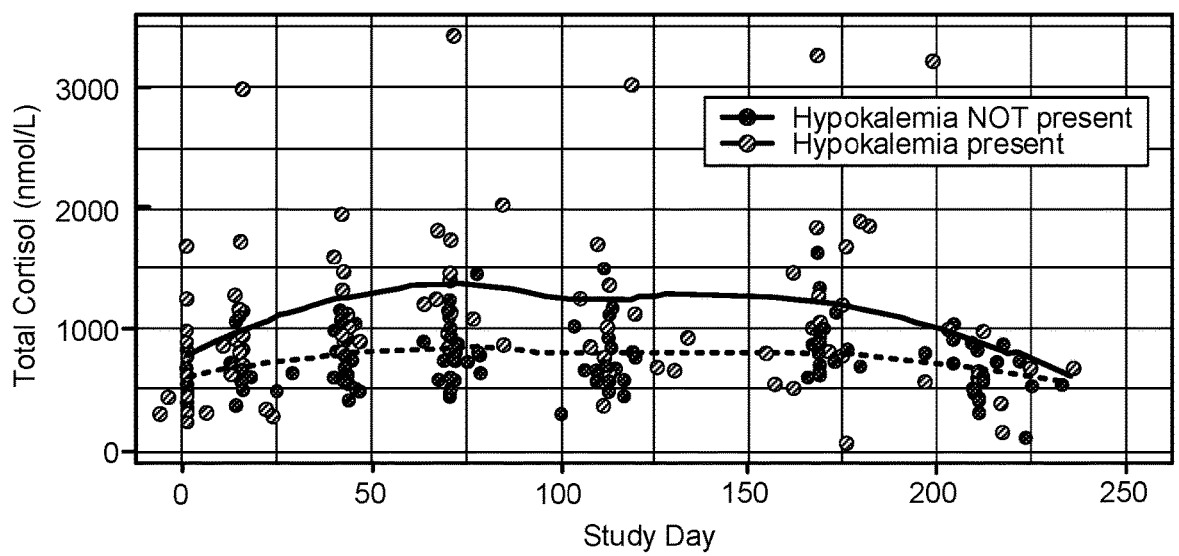
FIG. 2 demonstrates the association between levels of potassium (<3.5 mEq/L, ≥3.5 mEq/L) and Total Cortisol levels. It shows that patients with potassium levels<3.5 mEq/L had on average higher Total Cortisol levels on the same study day.

FIG. 2 demonstrates the association between levels of potassium (<3.5 mEq/L, ≥3.5 mEq/L) and Total Cortisol levels. It shows that patients with potassium levels<3.5 mEq/L had on average higher Total Cortisol levels on the same study day.

Hypokalemia with Dose Initiation of 300 mg/Day (Early-Onset Hypokalemia)

The risk of experiencing at least one episode of hypokalemia (potassium level<3.5 mEq/L) after 7 to 14 Days of exposure to KORLYM (mifepristone) was evaluated using stepwise multivariable logistic regression and single-variable logistic regression models. The following independent factors were evaluated for potential association with hypokalemia based on the biology of the disease: total cortisol at Day 1, ACTH at Day 1, and potassium level at Day 1.

The hypothesis that higher total cortisol levels at Day 1 are associated with post-baseline hypokalemia was supported by examining a variety of criteria for model fit across the models, including residuals, AIC (Akaike Information Criteria), BIC (Schwarz Bayesian Information Criterion), and associated ROC (Receiver Operating Characteristics) curves.

Results of the single-variable logistic regression with ACTH at Day 14 as an independent variable are presented below in Table 1.

TABLE 1

Maximum Likelihood Estimates of Logistic Regression Coefficients for the Odds of Early Hypokalemia

|  | Estimate | Standard Error | 95% CI Lower Limit | 95% CI Upper Limit | p-value |
|---|---|---|---|---|---|
| Intercept | −4.7856 | 1.5239 | −7.7723 | −1.7989 | 0.0017 |
| cort_01 | 0.00511 | 0.00211 | 0.000972 | 0.00926 | 0.0155 |

To determine the day-1 serum cortisol (cort_01) cut-off value that best differentiates patients at higher vs. lower risk for early hypokalemia, we considered both the points on the ROC curve which would balance sensitivity and specificity. If the ROC curve fitted to the observed data were exactly equal to the true ROC curve, then a value of 750 nmol/L at the Day 1 visit (see FIG. 3) would provide a good balance between sensitivity and specificity.

The estimated probabilities of developing early hypokalemia and associated sensitivity and specificity estimates were fitted to the observed data.

Table 2 summarizes the number of patients who experienced at least one episode of early hypokalemia by (Day 1 visit Total Cortisol (cort 01) level).

The performance of the identified cut-off using total serum cortisol level of 750 nmol/L results in a 6.8-fold increase in risk for patients with total serum cortisol>750 nmol/L level before KORLYM dosing compared with patients with total serum cortisol level≤750 nmol/L before KORLYM administration (58.3% vs. 8.6%, Fisher's Exact p-value≤0.0011). That is, seven (58.3%) of 12 patients with cort_01 values≥750 nmol/L developed early hypokalemia, (i.e., by the Day 7 or Day 14 visit), whereas 3 (8.6%) of 35 patients with cort_01 values<750 nmol/L developed early hypokalemia (Fisher's Exact test p-value=0.0011). This corresponds to a sensitivity of 70.0% and a specificity of 86.5%.

TABLE 2

Patients with Early Hypokalemia (at Day 7 or Day 14 visit), by Total Serum Cortisol Level at Day 1

| n (%) | No Early Hypokalemia (n = 37) | Early Hypokalemia (n = 10) | Total (n = 47) |
|---|---|---|---|
| Total cortisol, <750 nmol/L | 32 (86.5) | 3 (30.0) | 35 (74.5) |
| Total cortisol, ≥750 nmol/L | 5 (13.5) | 7 (70.0) | 12 (25.5) |

Hypokalemia, K <3.5 mmol/L.

Hypokalemia with Dose Escalation Above 300 mg/Day (Late-Onset Hypokalemia)

The risk of experiencing at least one episode of hypokalemia (potassium level<3.5 mmol/L) after 28 Days of exposure to KORLYM was evaluated using stepwise multivariable logistic regression and single-variable logistic regression models. The following independent factors were evaluated for potential association with hypokalemia based on the biology of the disease: total cortisol at Day 1 and Day 14 (cort 01 and cort 14), ACTH at Day 1 and Day 14 (ACTH_01 and ACTH_14), and potassium levels at Day 1 and Day 14 (K_01 and K_14).

ACTH levels at the Day 14 Visit are associated with the risk of developing subsequent hypokalemia during treatment with KORLYM at doses greater than 300 mg. This was supported by examining a variety of criteria for model fit across the models, including residuals, AIC (Akaike Information Criteria), BIC (Schwarz Bayesian Information Criterion), and associated ROC (Receiver Operating Characteristics) curves.

The single-variable logistic regression with ACTH at Day 14 as an independent variable shows a statistically significant association between the odds of developing late-onset hypokalemia and ACTH levels at Day 14 (p=0.0032. Results of the single-variable logistic regression with ACTH at Day 14 as an independent variable are presented below in Table 3, and the probabilities and odds of developing hypokalemia are presented below in Table 4.

TABLE 3

Maximum Likelihood Estimates of Logistic Regression Coefficients for the Odds of Hypokalemia

|  | Estimate | Standard Error | 95% CI Lower Limit | 95% CI Upper Limit | p-value |
|---|---|---|---|---|---|
| Intercept | −2.8357 | 0.8147 | −4.4325 | −1.2389 | 0.0005 |
| ACTH_14 | 0.0210 | 0.00713 | 0.00703 | 0.0350 | 0.0032 |

Using the above estimates, we note, for example, that the odds of developing hypokalemia increase more than 4-fold when ACTH level increase from 48 pg/mL (1' Quartile at Day 14) to 123 pg/mL ($3^{rd}$ quartile at Day 14):

TABLE 4

Increase in the Odds of Developing Hypokalemia

|  | Probability of Developing Hypokalemia, % | Odds of Developing Hypokalemia, % |
|---|---|---|
| ACTH = 48 mmol/L | 13.9 | 16.1 |
| ACTH = 123 mmol/L | 43.7 | 77.6 | where the odds are calculated by dividing (the probability of getting hypokalemia) by (the probability of not getting hypokalemia). For ACTH=48 mmol/L, the probability of getting hypokalemia is 13.9%; so the probability of not getting hypokalemia is 100%−13.9%=86.1%; the odds of getting hypokalemia with an ACTH of 48 mmol/L is then 13.9/(100−13.9)=16.1%. A similar calculation for ACTH=123 mmol/L shows that the odds of getting hypokalemia with an ACTH level of 123 mmol/L are 43.7/(100−43.7)=77.6%. The ratio of the odds for getting hypokalemia with an ACTH level of 123 mmol/L as compared to the odds for getting hypokalemia with an ACTH level of 48 mmol/L are then 77.6% divided by 16.1%=4.82. That is, the odds that a patient with an ACTH level of 123 mmol/L will suffer from hypokalemia are more than 4 times greater than the odds that a patient with an ACTH level of 48 mmol/L will suffer from hypokalemia.

To determine the ACTH cut-off value that best differentiates patients at higher risk from those at lower risk, we considered the points on the ROC curve that would balance sensitivity and specificity. Fitting the ROC curve to the observed data via a logistic regression model results in an ACTH value of 112 pg/mL at the Day 14 visit that provides a good balance between sensitivity and specificity. The ACTH_14 cut-off value of 112 pg/mL provides a high level of sensitivity of the ACTH-based test for predicting future hypokalemia, together with a low false-positive rate.

Figure 3:
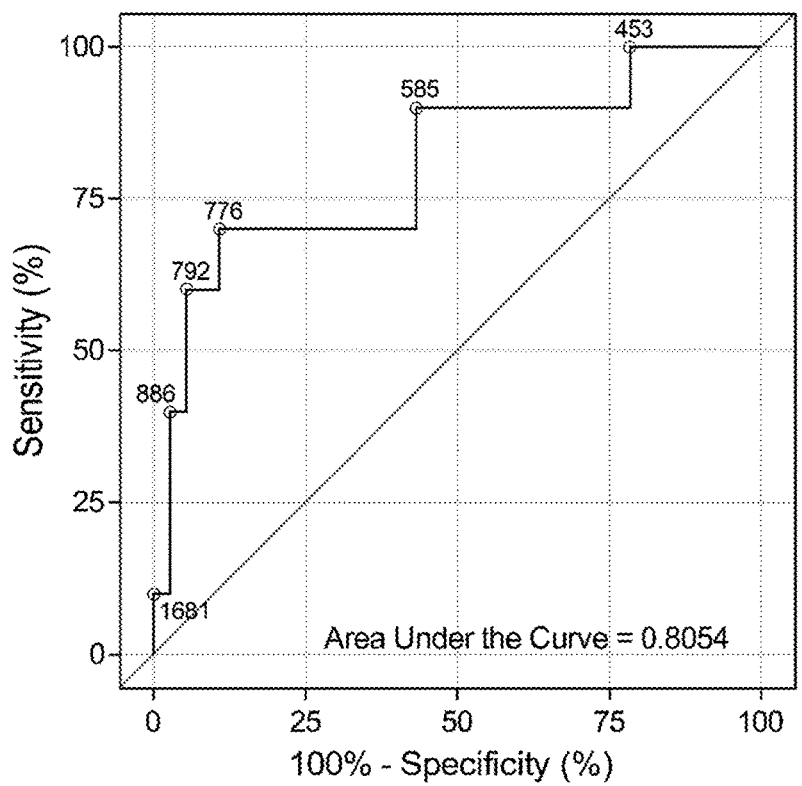
FIG. 3 ROC Curve for Association between Total Serum Cortisol at Baseline and Early-Onset Hypokalemia. Numbers on the corners of the ROC curve correspond to Baseline (Day 1) Serum Cortisol levels.
Figure 4:
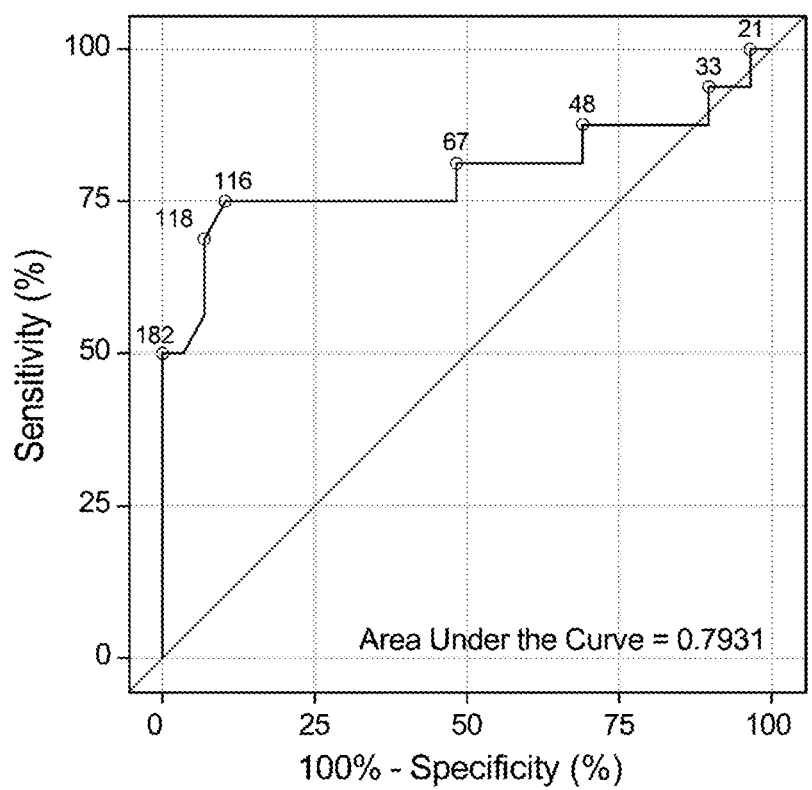
FIG. 4 ROC Curve for Association between ACTH at Day 14 and Subsequent Hypokalemia during Mifepristone Treatment.

The maximum likelihood estimates for developing hypokalemia and associated specificity estimates based on the model fitted to the observed data are presented in Tables 3 and 4 above as well as in FIGS. 3 and 4.

A sensitivity analysis using an ACTH cutoff of 112 pg/mL corresponding to a point on the ROC curve with an optimal balance of specificity and sensitivity results in a 6-fold (80% vs. 13.3%, Fisher's Exact p-value<0.0001) increase in risk for patients with ACTH levels above 112 pg/mL compared to patients with ACTH levels below 112 pg/mL.

Table 5 summarizes the number of patients who experience at least one episode of subsequent (post Day 28) hypokalemia by ACTH level during first 2 weeks. The performance of the identified cut-off using an ACTH level of 112 pg/mL corresponding to a point on the ROC curve with an optimal balance of specificity and sensitivity results in a 5.64-fold increase in risk for patients with ACTH>112 pg/mL at Day 14 compared with patients with ACTH≤112 pg/mL at Day 14 (75.0% vs. 13.3%, Fisher's Exact p-value<0.0001) (Table 2). This corresponds to a sensitivity of 75.0% and a specificity of 86.7%.

TABLE 5

Patients with Subsequent Hypokalemia, by ACTH after 2 Weeks of Treatment with KORLYM

|  | No Hypokalemia (n = 30) | Hypokalemia[a] n = 16 | Total (n = 46) |
|---|---|---|---|
| ACTH <112 pg/mL, n (%) | 26 (86.7) | 4 (25.0) | 30 (65.2) |
| ACTH ≥112 pg/mL, n (%) | 4 (13.3) | 12 (75.0) | 16 (21.7) |

[a]Potassium, <3.5 mmol/L.

Factors Associated with Severe/Recurrent Hypokalemia with Dose Escalation>300 mg/day Patients were defined to have severe/recurrent hypokalemia for this analysis if they had at least one value of potassium of 2.5 mmol/L or lower, or if they had recurrent hypokalemia (hypokalemia occurring during multiple visits after Day 14 visit). Nine (19.1%) of 47 patients experienced severe/recurrent hypokalemia, with two who had at least one potassium value of 2.5 mmol/L or lower, and all 9 had recurrent hypokalemia prior to or at the Week 24/Early termination visit.

To incorporate the above definition of severe/recurrent hypokalemia into the analysis, an ordinal hypokalemia response variable was defined as follows (over the previously defined time frame from the Day 14 visit to the Week 24/Early termination visit, inclusive):

2: Severe/recurrent Hypokalemia
1: Hypokalemia (Non-Severe)
0: No Hypokalemia

A Cochran-Mantel-Haenszel (CHM) test using an alternative hypothesis of "Row Mean Scores Differ" resulted in a corresponding p-value of 0.0017. It indicated that the Day 14 ACTH cutoff value of 112 pg/mL appears to be a useful threshold for distinguishing patients at higher risk for developing hypokalemia or severe/recurrent hypokalemia. Of 15 patients with high Day 14 visit ACTH values (>112 pg/mL) by Day 14, 5 (33.3%) developed subsequent hypokalemia at Day 28 or later, and 7 (46.7%) developed subsequent severe/recurrent hypokalemia (Table 6). Of the 30 patients with low ACTH values by Day 14, 2 (6.7%) of developed hypokalemia, and 2 (6.7%) developed severe/recurrent hypokalemia on or after Day 28 (CMH test p-value=0.0017).

TABLE 6

Number of Patients with Subsequent Hypokalemia or Severe/recurrent Hypokalemia within First 28 Days of Treatment with KORLYM, by Day 14 visit ACTH of 112 pg/mL

| n (%) | No Hypokalemia | Non-Severe Hypokalemia | Severe/ Recurrent Hypokalemia | Total |
|---|---|---|---|---|
| ACTH <112 pg/mL | 26 | 2 | 2 | 30 (67.7) |
| ACTH ≥112 pg/mL | 3 | 5 | 7 | 15 (33.3) |
| Total | 29 (64.4) | 7 (15.6) | 9 (20.0) | 45 (100) |

Effect of Potassium Supplements and Potassium-Sparing Agents

ACTH is a predictor of hypokalemia in patients regardless of treatment with anti-hypokalemic drugs.

The risk of developing hypokalemia after Day 14 was higher in patients with higher ACTH regardless whether they were treated prior to dosing with potassium supplements. Out of 14 patients who had been receiving treatment for hypokalemia before dosing with KORLYM, 6 (42.9%) developed hypokalemia after dosing with KORLYM. Of those, 5 (80%) patients had an ACTH>112 pg/mL on Day 14. The other 8 patients who had been receiving treatment for hypokalemia before dosing did not develop hypokalemia after dosing. Seven (87.5%) of these patients had ACTH level on Day 14≤112 pg/mL.

Patients at high risk should be treated with a sufficient dosage of potassium-sparing medications.

These conclusions hold regardless of whether patients were treated for hypokalemia with potassium supplements at baseline or at any point during the study.

Example 2

High Serum ACTH Levels Predict Hypokalemia

Clinical experience based on previous clinical studies of mifepristone administered to healthy volunteers identified headache, gastrointestinal symptoms including diarrhea, nausea and vomiting, and rash as frequently reported adverse events. Hypokalemia and rash appear to be more common in subjects receiving mifepristone than in the control groups.

In the data analysis presented in this Example, hypokalemia was defined as a potassium value≤3.4 mEq/L. When hypokalemia was reported as an adverse event (AE), the MedDRA dictionary coded the event as "decreased blood potassium." Seventeen subjects had reported treatment emergent adverse events (TEAEs) of decreased blood potassium. Three had reported TEAEs of hypokalemia but did not have corresponding laboratory values of low potassium recorded by the central laboratory.

Hypokalemia in the range of 2.4 to 3.4 mEq/L was seen in 61 of 782 (7.8%) mifepristone treated subjects and 19 of 584 (3.3%) placebo subjects in previously performed double blind psychotic major depression (PMD) trials. Hypokalemia in the range of 2.8 to 3.5 mEq/L was seen in 9 out of 33 subjects in an Alzheimer's study who had received 300 mg per day of mifepristone for 16 weeks. Out of 32 subjects in the placebo arm, none had a reported potassium level of 3.5 or lower. Clinically meaningful hypokalemia (≤3.1) has been reported in 16 of 821 (1.9%) mifepristone treated subjects (12 in completed double blind PMD trials, and 4 in a completed Alzheimer's trial), and in 5 of 626 (0.8%) placebo treated subjects in completed PMD trials.

The Cushing's syndrome study reported herein was conducted in accordance with the Declaration of Helsinki and Good Clinical Practice (GCP) according to International Conference on Harmonization (ICH) guidelines. Patients enrolled in the clinical study were men or non-pregnant women who are at least 18 years of age who required medical treatment for endogenous Cushing's syndrome due to ectopic ACTH syndrome, adrenal tumors, adrenal hyperplasia, and Cushing's disease, who were not candidates for pituitary surgery or who had failed or recurred after pituitary surgery or were otherwise not candidates for pituitary surgery.

Dosing Schedule Dosing was started with 300 mg of mifepristone once per day for 14 days. After 14 days, if no clinical improvement was seen but the drug was well tolerated, the dose of mifepristone was increased to 600 mg once per day. After 4 weeks of dosing at 600 mg once per day, if no clinical improvement was seen but the drug was well tolerated, the dose was increased to 900 mg once per day. Dose escalation was based on weight with the maximum dose no higher than 20 mg/kg/day. Subjects weighing<60 kg did not have the dose escalated beyond 900 mg once per day. After 4 weeks of dosing at 900 mg once per day, if no clinical improvement was seen but the drug was well tolerated, the dose was increased to 1200 mg once per day. Study duration was 24 weeks.

Serum electrolytes, including potassium, were measured regularly throughout the study period. A patient was considered to have hypokalemia if the patient's potassium level fell below 3.5 mEq/L. Decreased potassium was observed during at least one visit in 17 of 34 patients during the study (about 30%), some of these patients had hypokalemia (potassium levels below 3.5 mEq/L) or edema.

47 subjects were part of either Etiology Group 1 (N=43, Cushing Syndrome) or Etiology Group 2 (N=4, Ectopic). In these 47 suybjects, There were 21 subjects total who had a Potassium value≤3.5 mmol/L, at any of the six visits listed below. Therefore, 8 of the 21 (38%) had a Potassium value≤3.5 mmol/L as early as day 14. They are: 007-010, 008-014, 010-002, 011-003, 011-004, 015-005, 018-001, 024-001.

Further, there were 23 subjects total who had a Potassium value≤3.5 mmol/L, at any post-baseline visit. Of these 23 subjects, there were three subjects with a day 7, Potassium value≤3.5 mmol/L. They are 015-002 and 020-002, 022-001, and 8 different subjects with a day 14 Potassium value≤3.5 mmol/L Thus, there were a total of 11 (48%) of 23 subjects with a Potassium value≤3.5 mmol/L as early as day 14, taking all post-baseline values into consideration.

Hypokalemia was generally mild to moderate and was often associated with alkalosis (elevated CO2) and variably associated with edema. The hypokalemia responded to treatment with potassium supplementation; mineralocorticoid antagonists were also used. The doses of potassium supplements for these subjects ranged from 10 mEq daily to 340 mEq daily and doses of spironolactone ranged from 50 mg to 300 mg daily. Four subjects had potassium values that met the definition of severe hypokalemia (≤2.5 mEq/L). In three of the four instances, there were previous potassium values that were low, although not in the severe hypokalemic range, and these subjects were receiving treatment with potassium; two were taking spironolactone. The potassium level increased after the episode of severe hypokalemia. Severe hypokalemia in one subject occurred at the follow-up visit when the subject had not been taking mifepristone for 6 weeks.

Summary of Subjects with Hypokalemia (Potassium≤3.4 mEq/L) and Severe Hypokalemia (Potassium≤2.5 mEq/L)

A summary of subjects with hypokalemia (serum potassium≤3.4 mEq/L [≤3.4 mmol/L]) and severe hypokalemia (serum potassium≤2.5 mEq/L [≤2.5 mmol/L]) is presented in Table 7. Subjects were included in this table based on serum potassium values from laboratory testing, regardless of whether they had a reported adverse event (AE) with a preferred term of "decreased blood potassium" (three subjects had treatment emergent adverse events (TEAEs) of hypokalemia without corresponding low potassium values).

TABLE 7

Summary of Subjects with Hypokalemia and Severe Hypokalemia
Hypokalemia: Potassium ≤3.4 mEq/L); Severe Hypokalemia:
Potassium ≤2.5 mEq/L

| Treatment day or week of [K] measurement | Number with Hypokalemia (%) (Potassium ≤3.4 mEq/L) | Number with Severe Hypokalemia (%) (Potassium ≤2.5 mEq/L) |
|---|---|---|
| Screen (prior to treatment) | 5 (10%) | |
| Day 1 | 2 (4%) | |
| Day 7 | 2 (4%) | |
| Day 14 | 8 (16%) | 1 (2%) |
| Day 28 | 10 (20%) | |
| Week 6 | 7 (14%) | |
| Week 8 | 4 (8%) | |
| Week 10 | 4 (8%) | |
| Week 12 | 3 (6%) | 1 (2%) |
| Week 16 | 5 (10%) | 1 (2%) |
| Week 20 | 1 (2%) | |
| Week 24/Early Termination | 4 (8%) | |
| 6 Week Follow-Up | 3 (6%) | 1 (2%) |

Note:
Subjects having Severe Hypokalemia are also included with subjects having Hypokalemia
Overall Number of Subjects N = 50

Hypokalemia was generally mild to moderate and was often associated with alkalosis (elevated $CO_2$) and variably associated with edema. The hypokalemia responded to treatment with potassium supplementation; mineralocorticoid antagonists were also used. The doses of potassium supplements for these subjects ranged from 10 mEq daily to 340 mEq daily and doses of spironolactone ranged from 50 mg to 300 mg daily. Four subjects had potassium values that met the definition of severe hypokalemia (≤2.5 mEq/L): Subject 06-003 (at 6-week follow-up), Subject 07-010 (at Week 16), Subject 15-005 (at Day 14), and Subject 18-001 (at Week 12). In three of the four instances (not for Subject 15-005), there were previous potassium values that were low, although not in the severe hypokalemic range, and these subjects were receiving treatment with potassium; two were taking spironolactone (Subjects 07-010 and 18-001). The potassium level increased after the episode of severe hypokalemia. The severe hypokalemia for Subject 06-003 occurred at the follow-up visit when the subject had not been taking mifepristone for 6 weeks.

Hypokalemia can be related to elevations in cortisol that occur when ACTH rises as a result of glucocorticoid blockade produced by mifepristone. As cortisol levels rise, the normal mechanism to inactivate cortisol in the kidney is saturated (11-hydroxysteroid dehydrogenase type 2) and the mineralocorticoid receptor is activated. This state of apparent mineralocorticoid excess leads to hypokalemia (presumably from accentuated kaliuresis) as well as alkalosis, and edema. In this study, most cases of hypokalemia occurred early in the course of treatment. Hypokalemia responded to medical therapy, which often consisted of large amounts of supplemental potassium and mineralocorticoid antagonists. The episodes of severe hypokalemia were preceded by declining potassium levels, indicating that aggressive early intervention might prevent severe episodes.

The levels of ACTH and cortisol increased in most subjects during mifepristone treatment. Subjects with Cushing's disease could have increased ACTH production due to loss of a negative feedback loop with glucocorticoid receptor blockade. Patients who have had pituitary surgery to treat Cushing's disease and who later undergo adrenalectomy because of persistent hypercortisolism have a risk of increased pituitary tumor volume when cortisol levels drop after adrenal surgery. Although the mechanism for increased pituitary volume after adrenalectomy is not completely understood, increased tumor volume may occur due to the absence of negative feedback on the tumoral corticotrophs; ACTH rises due to lack of negative feedback on its production by cortisol. Theoretically, the same problem could arise with mifepristone treatment because glucocorticoid blockade stops the negative feedback that controls ACTH levels. In the 43 subjects with Cushing's disease, ACTH increased about two-fold and serum cortisol increased to a smaller degree during mifepristone treatment.

Adverse events such as hypokalemia associated in some patients with mifepristone treatment can be, and for these patients was, managed, e.g., by potassium supplementation, administration of spironolactone, or other measures.

FIG. 1 shows the serum ACTH level of Cushing's syndrome patients receiving mifepristone treatment. The upper curve presents the serum ACTH level of those Cushing's syndrome patients who experienced hypokalemia during the course of treatment (patients also received therapy for the hypokalemia as needed). The lower curve presents the serum ACTH level of those Cushing's syndrome patients who did not experience hypokalemia during the course of treatment. Note that the two curves are clearly separate at the second time point (14 days) when patients, who had been receiving 300 mg mifepristone per day from day 0 to day 13, began receiving 600 mg mifepristone at day 14 and after. Thus, those patients who experienced hypokalemia can be identified very early on during treatment, and therapy for hypokalemia administered, even in the absence of low potassium at that time.

As shown in FIG. 1, Cushing's syndrome patients who experienced hypokalemia during the course of their mifepristone treatment were those patients whose ACTH levels rose above about 100 pg/mL (e.g., above about 112 pg/mL). Cushing's syndrome patients who experienced hypokalemia during the course of their mifepristone treatment exhibited ACTH levels above about 150 pg/mL, and above about 200 pg/mL, and above about 250 pg/mL. In contrast, those Cushing's syndrome patients whose ACTH levels did not rise above about 100 pg/mL (e.g., remained below about 112 pg/mL, and remained below about 150 pg/mL) did not experience hypokalemia during the course of their mifepristone treatment.

These results allow the identification of Cushing's syndrome patients at risk for developing hypokalemia during mifepristone treatment for Cushing's syndrome. These results allow the differentiation between those Cushing's syndrome patients at risk for developing hypokalemia during mifepristone treatment for Cushing's syndrome and those Cushing's syndrome patients at lower, or at no, risk for developing hypokalemia during mifepristone treatment for Cushing's syndrome. Such identification and differentiation allows for providing preventive therapy for hypokalemia to those patients at most risk for hypokalemia, in advance of low potassium and so in advance of deleterious and potentially life-threatening symptoms. In addition, such identification and differentiation allows treating physicians to avoid providing unneeded hypokalemia therapy to those patients at least risk, or at no risk, for hypokalemia, thus avoiding any potential side-effects from such treatment.

Example 3

Increased ACTH Levels Following Mifepristone Dose Increase Predict Hypokalemia

Further inspection of FIG. 1 shows that the serum ACTH level of Cushing's syndrome patients showed different types of responses to increases in mifepristone dosage. The upper curve (showing the serum ACTH level of those Cushing's syndrome patients who experienced hypokalemia) is not only higher, but also more irregularly shaped: this indicates that these patients reacted more sharply to increases in mifepristone dose (even at later time periods than at the early, day 14 measurements) than did patients who did not experience hypokalemia during the course of treatment.

Extensive modeling of low potassium levels among the N=47 subjects was performed to determine the best predictors of low potassium after start of mifepristone. The modeling was based on logistic regressions where the endpoint was categorical Low vs High Potassium levels (Non-Hypokalemic Potassium>3.5 mmol/L vs Hypokalemic Potassium≤3.5 mmol/L).

Potassium levels were obtained on every subject at either screening or the pre-drug administration baseline visit, and then also at every scheduled post-baseline visit. Potassium levels post-baseline were therefore obtained as early as day 7 and through day 210 (week 30 was the last visit and was the 6 week follow-up visit). ACTH, and cortisol were measured at six visits (week 2 (day 14), week 6 (day 42), week 10 (day 70), week 16 (day 112), and week 24 (day 168) week 6 follow-up (day 210)).

The logistic regression modeling was performed based on baseline ACTH, day 14 ACTH levels, and change at day 14 from baseline for ACTH. The modeling was performed to find the best statistically significant predictor with a sufficiently high sensitivity and specificity to predict which patients might be at risk for developing low potassium levels.

A stepwise logistic regression model predicting potassium levels≤3.5 mmol/L at any post-week 2 visit, based on only baselines and week 2 variables (ACTH, cortisol, cortisol/ACTH ratio and potassium) showed that ACTH at day 14 (SAS derived variable name ACTH14) was a statistically significant predictor of low potassium levels (P=0.0005, c-statistic=0.687).

A simple logistic regression analysis was further performed using only ACTH on day 14 as the single independent predictor of low potassium levels at any post-week 2 visit. ACTH on day 14 was highly statistically significant (P<0.0001, c-statistic=0.673). In addition, we produced the ROC table showing for each value of ACTH14, the sensitivity and specificity. The estimated threshold was determined where sensitivity and specificity are approximately equal at 108 mmol/L. Thus, ACTH greater than about 100 pg/mL was a good predictor of later hypokalemia.

Further analyses confirm the usefulness of ACTH levels in predicting hypokalemia in Cushing's syndrome patients later on during therapy. Cross classification results by binary category of potassium level at the respective visit and the ACTH category at Day 14 were examined. On Day 28, of the 9 subjects with a low potassium, the logistic regression model based only on the ACTH at day 14, predicts 7 of the 9 (77.8%) subjects with a low potassium level (Chi-squared P=0.007). Day 28, is the best cross classification result. There were other fairly successful predictions on designated visits. On day 42, ACTH on day 14, predicts 4 of the 6 (66.7%) subjects with a low potassium level (Chi-squared P=0.069). On day 42, ACTH on day 14, predicts 4 of the 6 (66.7%) subjects with a low potassium level (Chi-squared P=0.069). On day 168 (week 24), ACTH on day 14, predicts 4 of 5 (80%) of the subjects with a low potassium level (Chi-squared P=0.045).

As shown in FIG. 1, Cushing's syndrome patients who experienced hypokalemia during the course of their mifepristone treatment were those patients whose ACTH levels rose by about 50 pg/mL to 100 pg/mL following an initial increase in mifepristone dose. In contrast, those Cushing's syndrome patients who did not experience hypokalemia were those whose ACTH levels rose by only about 25 pg/mL following an initial increase in mifepristone dose. The FIGURE further shows that ACTH levels of Cushing's patients who experienced hypokalemia also rose (by about 75 pg/mL to about 100 pg/mL) following subsequent increases in mifepristone dose (see, e.g., day 70, and day 168). In contrast, no such dramatic rises in ACTH levels following mifepristone dose increases were seen in Cushing's patients who did not experience hypokalemia rose.

Thus, those patients who experienced hypokalemia can be identified not only by the levels of ACTH measured in their blood, but also by the more pronounced changes (increases) in ACTH levels following mifepristone dose increases. This second identifying characteristic, which appears very early on during treatment, and also at later times during treatment, allows for preventive therapy for hypokalemia to be administered when the signal is recognized, even in the absence of low potassium at that time.

Example 4

ACTH Visit Change Values from Baseline Predict Hypokalemia

Comparison of ACTH visit change values from baseline shows significant differences between non-hypokalemic Cushing's syndrome patients and those Cushing's syndrome patients who experienced hypokalemia during the study period. The difference in change values seen between non-hypokalemic and hypokalemic patients by treatment day 70 allows prophylactic treatment relatively early on during treatment, in order to prevent the development of, or worsening of, and to allow reversal of, hypokalemia in those patients identifiable by the high ACTH visit change values at day 70 (e.g., patients with ACTH visit change values of about 200 ng/L or above). Patients were from both Etiology Group 1 (pituitary Cushing's disease) and from Etiology Group 2 (ectopic Cushing's) (N=47).

TABLE 8

ACTH (ng/L) Visit Change Values from Baseline

| Mean ± SD (N) | Non-Hypokalemic | Hypokalemic | t-test P-Value |
| --- | --- | --- | --- |
| Day 14  | 30.6 ± 26.9 (38) | 60.8 ± 99.6 (8)  | 0.1 |
| Day 42  | 40.6 ± 54.7 (35) | 86.3 ± 58.2 (6)  | 0.07 |
| Day 70  | 49.2 ± 22.5 (30) | 211.8 ± 147.5 (6) | 0.0002 |
| Day 112 | 70.2 ± 82.2 (23) | 101.4 ± 159.6 (9) | 0.5 |
| Day 168 | 48.2 ± 73.8 (37) | 151.2 ± 166.5 (5) | 0.02 |
| Day 210 | 13.4 ± 34.0 (37) | 113.7 ± 167.7 (3) | 0.002 |

Thus, those patients who experienced hypokalemia can be identified by comparison of the ACTH change values with the ACTH baseline value. This further identifying characteristic further allows for preventive therapy for hypokalemia to be administered when the signal is recognized, even in the absence of low potassium at that time.

Example 5

ACTH Visit Change Values from Baseline Predict Hypokalemia

Comparison of the ratio of ACTH visit change values from baseline divided by baseline ACTH value shows significant differences between non-hypokalemic Cushing's syndrome patients and those Cushing's syndrome patients who experienced hypokalemia during the study period. Thus, at visit day 70, those patients who experienced hypokalemia can be identified by comparison of the ratio of ACTH visit change values from baseline divided by the ACTH baseline value. This further identifying characteristic further allows for preventive therapy for hypokalemia to be administered when the signal is recognized, even in the absence of low potassium at that time.

TABLE 9

Ratio of ACTH Visit Change Values from Baseline per Baseline Etiology Groups 1 and 2 (N = 47)

| Mean ± SD (N) ACTH_CHG/ ACTH Baseline | Non-Hypokalemic | Hypokalemic | t-test P-Value |
|---|---|---|---|
| Day 14 | 1.77 ± 0.72 (38) | 1.87 ± 1.32 (8) | 0.8 |
| Day 42 | 2.02 ± 0.97 (35) | 2.50 ± 0.61 (6) | 0.3 |
| Day 70 | 2.06 ± 1.01 (30) | 4.08 ± 2.51 (6) | 0.002 |
| Day 112 | 2.47 ± 1.87 (23) | 2.53 ± 1.49 (9) | 0.9 |
| Day 168 | 2.08 ± 1.31 (37) | 3.30 ± 2.54 (5) | 0.09 |
| Day 210 | 1.33 ± 0.61 (37) | 1.36 ± 0.46 (3) | 0.9 |

Similar differentiation between Cushing's patients who experienced hypokalemia during mifepristone treatment, and those who did not, was also obtained by calculating the ratio of ACTH level at a particular visit day divided by ACTH baseline level (i.e., essentially the same P-value results are seen if the ratio is defined as ACTH/ACTH baseline).

Example 6

Total Serum Cortisol Visit Values Predict Hypokalemia

Comparison of Total Serum cortisol (nmol/L) visit values shows significant differences between non-hypokalemic Cushing's syndrome patients and those Cushing's syndrome patients who experienced hypokalemia during the mifepristone treatment study period.

TABLE 10

Total Serum Cortisol (nmol/L) Visit Values

| Mean ± SD (N) | Non-Hypokalemic | Hypokalemic | t-test P-Value |
|---|---|---|---|
| Day 14 | 782 ± 246 (38) | 1261 ± 786 (8) | 0.002 |
| Day 42 | 828 ± 249 (35) | 1274 ± 401 (6) | 0.0007 |
| Day 70 | 1025 ± 546 (30) | 1390 ± 283 (6) | 0.1 |
| Day 112 | 813 ± 318 (23) | 1318 ± 677 (9) | 0.007 |
| Day 168 | 948 ± 537 (37) | 1298 ± 597 (5) | 0.2 |
| Day 210 | 696 ± 477 (37) | 1228 ± 561 (3) | 0.07 |

As shown in Table 10, Cushing's syndrome patients who experienced hypokalemia during the course of their mifepristone treatment were those patients whose total serum cortisol levels were above about 1000 nmol/L (e.g., above about 1100 nmol/L, or about 1200 nmol/L) early on during mifepristone treatment (e.g., day 14 and day 42). In contrast, Cushing's syndrome patients who did not experience hypokalemia had total serum cortisol levels below about 1000 nmol/L (e.g., below about 900 nmol/L, or below about 800 nmol/L) early on during mifepristone treatment (e.g., at day 14 and/or day 42). Such differences also persisted throughout the treatment period, with hypokalemia patients having total serum cortisol levels above about 1000 nmol/L (e.g., above about 1100 nmol/L, or about 1200 nmol/L) throughout the treatment period, and even above about 1300 nmol/L on day 112. In contrast, Cushing's syndrome patients who did not experience hypokalemia had total serum cortisol levels below about 1000 nmol/L on every measurement day except day 70; and had total serum cortisol levels below about 900 nmol/L on all other days throughout the mifepristone treatment period.

Thus, Cushing's patients who experienced hypokalemia were those whose total serum cortisol was high at early time during treatment, allowing early identification and differentiation of those Cushing's patients at risk for developing hypokalemia, and allowing early intervention with hypokalemia therapy in order to avoid, or reduce the severity of, and eventually to reverse, hypokalemia in Cushing's syndrome patients receiving mifepristone treatment.

Thus, measurement of total serum cortisol can also be used to determine the risk for, and to identify those patients at risk for, hypokalemia, and by providing early hypokalemia therapy, may prevent or ameliorate hypokalemia in Cushing's syndrome patients receiving mifepristone therapy. This yet further identifying characteristic, which appears very early on during treatment, and also at later times during treatment, allows for preventive therapy for hypokalemia to be administered when the signal is recognized, even in the absence of low potassium at that time.

Example 7

24-Hour Urine Cortisol Visit Values Predict Hypokalemia

Comparison of 24-hour Urine cortisol (nmol/24 hour) visit values shows significant differences between non-hypokalemic Cushing's syndrome patients and those Cushing's syndrome patients who experienced hypokalemia during the study period.

TABLE 11

24 Hour Urine Cortisol (nmol/24 hr) Visit Values Etiology Groups 1 and 2 (N = 47)

| Mean ± SD (N) | Non-Hypokalemic | Hypokalemic | t-test P-Value |
|---|---|---|---|
| Day 42 | 886 ± 1060 (35) | 4373 ± 5347 (6) | 0.0007 |
| Day 70 | 1696 ± 3387 (30) | 9132 ± 9321 (6) | 0.002 |
| Day 112 | 1314 ± 3351 (23) | 3552 ± 2827 (9) | 0.09 |
| Day 168 | 1444 ± 3127 (36) | 5615 ± 5053 (5) | 0.01 |
| Day 210 | 1423 ± 6086 (35) | 5129 ± 6335 (3) | 0.3 |

As shown in Table 11, Cushing's syndrome patients who experienced hypokalemia during the course of their mifepristone treatment were those patients whose 24-hour urine cortisol levels were above about 2000 nmol/24 hr (e.g., above about 2500 nmol/24 hr, or above about 3000 nmol/24 hr, or above about 4000 nmol/24 hr, or above about 5000 nmol/24 hr, or above about 6000 nmol/24 hr, or above about 7000 nmol/24 hr, or above about 8000 nmol/24 hr, or above about 9000 nmol/24 hr, all of which 24 hour urine cortisol levels are above those found for Cushing's syndrome patients who did not experience hypokalemia). The 24 hour urine cortisol measurements are different between the two groups of patients fairly early during mifepristone treatment (e.g., day 42 and day 70) and allow early identification of patients at risk. (No 24 hour urine cortisol measurement was obtained on day 7 of the study.) In contrast to the Cushing's patients who experienced hypokalemia, Cushing's syndrome patients who did not experience hypokalemia had 24 hour urine cortisol levels below about 1700 nmol/24 hr (e.g., below about 1000 nmol/24 hr) at all times during mifepristone treatment.

Thus, Cushing's patients who experienced hypokalemia were those whose 24 hour urine cortisol levels were high at early, and at all, times during treatment, allowing early identification and differentiation of those Cushing's patients at risk for developing hypokalemia, and allowing early intervention with hypokalemia therapy in order to avoid, or reduce the severity of, and eventually to reverse, hypokalemia in Cushing's syndrome patients receiving mifepristone treatment. Thus, measurement of 24 hour urine cortisol levels can also be used to determine the risk for, and to identify those patients at risk for, hypokalemia, and by providing early hypokalemia therapy, may prevent or ameliorate hypokalemia in Cushing's syndrome patients receiving mifepristone therapy. This yet further identifying characteristic, which appears very early on during treatment, and also at later times during treatment, allows for preventive therapy for hypokalemia to be administered when the signal is recognized, even in the absence of low potassium at that time.

Thus, in embodiments, Applicant discloses methods for treating an adult patient with endogenous Cushing's syndrome having type 2 diabetes mellitus or glucose intolerance to control hyperglycemia secondary to hypercortisolism and for reducing the risk of/preventing the development of hypokalemia in the patient, the methods comprising: a) administering to the patient an effective amount of a therapeutic agent for treating hypokalemia, wherein the patient is one whose 24-hour urine cortisol levels were above about 2000 nmol/24 hr (e.g., above about 2500 nmol/24 hr, or above about 3000 nmol/24 hr, or above about 4000 nmol/24 hr, or above about 5000 nmol/24 hr, or above about 6000 nmol/24 hr, or above about 7000 nmol/24 hr, or above about 8000 nmol/24 hr, or above about 9000 nmol/24 hr, and wherein the patient does not have a lower than normal potassium level; whereby the patient is treated to control hyperglycemia secondary to hypercortisolism and the risk of developing hypokalemia is reduced or hypokalemia is prevented in the patient. The therapeutic agent for treating hypokalemia may be, e.g., a mineralocorticoid receptor antagonist (e.g., spironolactone) or a potassium supplement. In embodiments, step (a) comprises administering to the patient the therapeutic agent for hypokalemia just before, or at about the same time as, administering to the patient a second and higher dose of GRM. In embodiments, the first dose of GRM has been administered to the patient prior to step (a), e.g., for at least two weeks. In embodiments, the GRM is mifepristone; wherein the first dose of mifepristone is 300 mg/day, 600 mg/day, or 900 mg/day of mifepristone. In embodiments, the patient has failed surgery, or is not a candidate for surgery, for Cushing's syndrome. In embodiments, the methods further include, prior to step (a), the steps of: (i) administering to the patient at least once the first dose of GRM; and (ii) obtaining a blood sample from the patient to determine the patient's morning serum ACTH level. cortisol level.

Example 8

24-Hour Urine Cortisol Visit Change Values from Baseline Predict Hypokalemia

Comparison of 24-hour Urine cortisol (nmol/24 hour) visit change values from baseline shows significant differences non-hypokalemic Cushing's syndrome patients and those Cushing's syndrome patients who experienced hypokalemia during the study period.

TABLE 12

24 Hour Urine Cortisol (nmol/24 hr) Visit Change Values from Baseline Etiology Groups 1 and 2 (N = 47)

| Mean ± SD (N) | Non-Hypokalemic | Hypokalemic | t-test P-Value |
|---|---|---|---|
| Day 42 | 329 ± 967 (35) | 641 ± 3678 (6) | 0.7 |
| Day 70 | 1045 ± 3500 (30) | 4856 ± 4805 (6) | 0.04 |
| Day 112 | 104 ± 5293 (23) | 2916 ± 2593 (9) | 0.1 |
| Day 168 | 512 ± 4575 (36) | 4128 ± 6624 (5) | 0.1 |
| Day 210 | 471 ± 2843 (35) | 2497 ± 3776 (3) | 0.3 |

As shown in Table 12, Cushing's syndrome patients who experienced hypokalemia during the course of their mifepristone treatment were those patients whose change in 24-hour urine cortisol levels (as compared to their baseline 24-hour urine cortisol levels) was greater than about 600 nmol/24 hr on day 42, and higher (e.g., greater than about 4000 or about 5000 nmol/24 hr on day 70). Such change in 24-hour urine cortisol levels (as compared to their baseline 24-hour urine cortisol levels) was greater than that observed for Cushing's syndrome patients who did not experience hypokalemia during the course of their mifepristone treatment.

Thus, change in 24-hour urine cortisol levels (as compared to their baseline 24-hour urine cortisol levels) is another differentiating factor that may be used to identify Cushing's syndrome patients at risk for hypokalemia. This differentiating factor may also be used to identify and differentiate between the two groups of patients, and to allow early identification of patients at risk. Such identification of those Cushing's patients at risk for developing hypokalemia allows the early intervention with hypokalemia therapy in order to avoid, or reduce the severity of, and eventually to reverse, hypokalemia in Cushing's syndrome patients receiving mifepristone treatment.

Thus, in embodiments, Applicant discloses methods for treating an adult patient with endogenous Cushing's syndrome having type 2 diabetes mellitus or glucose intolerance to control hyperglycemia secondary to hypercortisolism and for reducing the risk of/preventing the development of hypokalemia in the patient, the methods comprising: a) administering to the patient an effective amount of a therapeutic agent for treating hypokalemia, wherein the patient prior to step (a) has been administered at least once a first dose of glucocorticoid receptor modulator (GRM) and the change in the patient's 24-hour urinary cortisol levels as compared to their baseline 24-hour urinary cortisol levels) was greater than about 600 nmol/24 hr on day 42, and higher (e.g., greater than about 4000 or about 5000 nmol/24 hr on day 70), and wherein the patient does not have a lower than normal potassium level; whereby the patient is treated to control hyperglycemia secondary to hypercortisolism and the risk of developing hypokalemia is reduced or hypokalemia is prevented in the patient. The therapeutic agent for treating hypokalemia may be, e.g., a mineralocorticoid receptor antagonist (e.g., spironolactone) or a potassium supplement. In embodiments, step (a) comprises administering to the patient the therapeutic agent for hypokalemia just before, or at about the same time as, administering to the patient a second and higher dose of GRM. In embodiments, the first dose of GRM has been administered to the patient prior to step (a), e.g., for at least two weeks. In embodiments, the GRM is mifepristone; wherein the first dose of mifepristone is 300 mg/day, 600 mg/day, or 900 mg/day of mifepristone. In embodiments, the patient has failed surgery, or is not a candidate for surgery, for Cushing's syndrome. In embodiments, the methods further include, prior to step (a), the steps of: (i) administering to the patient at least once the first dose of GRM; and (ii) obtaining a blood sample from the patient to determine the patient's morning serum ACTH level. cortisol level.

Example 9

24-Hour Urine Cortisol Divided by ACTH Predicts Hypokalemia

Comparison of the ratios of 24-hour Urine cortisol (nmol/24 hour) divided by ACTH visit values from baseline shows significant differences non-hypokalemic Cushing's syndrome patients and those Cushing's syndrome patients who experienced hypokalemia during the study period.

TABLE 13

24 Hour Urine Cortisol (nmol/24 hr)/ACTH Ratio Visit Values Etiology Groups 1 and 2 (N = 47)

| Mean ± SD (N) | Non-Hypokalemic | Hypokalemic | t-test P-Value |
|---|---|---|---|
| Day 42 | 7.9 ± 6.0 (35) | 26.1 ± 18.4 (6) | 0.0001 |
| Day 70 | 17.0 ± 32.7 (30) | 33.5 ± 16.1 (6) | 0.3 |
| Day 112 | 9.6 ± 16.3 (23) | 30.9 ± 31.0 (9) | 0.02 |
| Day 168 | 12.4 ± 15.5 (36) | 19.3 ± 9.5 (5) | 0.3 |
| Day 210 | 12.5 ± 27.9 (35) | 11.5 ± 7.5 (3) | 0.9 |

As shown in Table 13, the ratio of 24-hour urine cortisol value divided by the ACTH level measured at the same visit day can be used to differentiate between Cushing's syndrome patients who experienced hypokalemia during the course of their mifepristone treatment and Cushing's syndrome patients who did not experience hypokalemia during the course of their mifepristone treatment. Cushing's syndrome patients experiencing hypokalemia had ratios of 24-hour urine cortisol values divided by ACTH values greater than about 20 (e.g., greater than about 25, or greater than about 30, or greater than about 35). In contrast, Cushing's syndrome patients who did not experience hypokalemia had ratios of 24-hour urine cortisol values divided by ACTH values less than about 20 (e.g., less than about 15 on most days, and less than about 10 on days 42 and 112).

Thus, the ratio of 24-hour urine cortisol values divided by ACTH values is another differentiating factor that may be used to identify Cushing's syndrome patients at risk for hypokalemia. This differentiating factor may also be used to identify and differentiate between the two groups of patients, and to allow early identification of patients at risk. Such identification of those Cushing's patients at risk for developing hypokalemia allows the early intervention with hypokalemia therapy in order to avoid, or reduce the severity of, and eventually to reverse, hypokalemia in Cushing's syndrome patients receiving mifepristone treatment.

Thus, in embodiments, Applicant discloses methods for treating an adult patient with endogenous Cushing's syndrome having type 2 diabetes mellitus or glucose intolerance to control hyperglycemia secondary to hypercortisolism and for reducing the risk of/preventing the development of hypokalemia in the patient, the methods comprising: a) administering to the patient an effective amount of a therapeutic agent for treating hypokalemia, wherein the patient prior to step (a) has been administered at least once a first dose of glucocorticoid receptor modulator (GRM) and the ratio of the patient's 24-hour urinary cortisol divided by the patient's serum ACTH level is at least about 20, and wherein the patient does not have a lower than normal potassium level; whereby the patient is treated to control hyperglycemia secondary to hypercortisolism and the risk of developing hypokalemia is reduced or hypokalemia is prevented in the patient. The therapeutic agent for treating hypokalemia may be, e.g., a mineralocorticoid receptor antagonist (e.g., spironolactone) or a potassium supplement. In embodiments, step (a) comprises administering to the patient the therapeutic agent for hypokalemia just before, or at about the same time as, administering to the patient a second and higher dose of GRM. In embodiments, the first dose of GRM has been administered to the patient prior to step (a), e.g., for at least two weeks. In embodiments, the GRM is mifepristone; wherein the first dose of mifepristone is 300 mg/day, 600 mg/day, or 900 mg/day of mifepristone. In embodiments, the patient has failed surgery, or is not a candidate for surgery, for Cushing's syndrome. In embodiments, the methods further include, prior to step (a), the steps of: (i) administering to the patient at least once the first dose of GRM; and (ii) obtaining a blood sample from the patient to determine the patient's morning serum ACTH level. cortisol level.

Example 10

Numbers of Subjects with Potassium Values Less Than or Equal to 3.5 mEq/L

There were 21 subjects total who had a Potassium values<=3.5 mmol/L, at any of the six visits listed below. Therefore, 8 of the 21 (38%) had a Potassium value≤=3.5 mmol/L as early as day 14. They are: 007-010, 008-014, 010-002, 011-003, 011-004, 015-005, 018-001, 024-001. Further, there were 23 subjects total who had a Potassium values<=3.5 mmol/L, at any post-baseline visit. Of these 23 subjects, there were three subjects with a day 7, Potassium value<=3.5 mmol/L. They are 015-002 and 020-002, 022-001, and 8 different subjects with a day 14 Potassium value≤=3.5 mmol/L Thus, there were a total of 11 (48%) of 23 subjects with a Potassium value≤=3.5 mmol/L as early as day 14, taking all post-baseline values into consideration. There were 4 subjects total (all in Etiology group 1) who had Potassium values<=2.5 mmol/L; Subject 006-003 had a potassium value of 2.5 at the 6 week follow up (day 210), Subject 007-010 had a potassium value of 2.1 at the week 16 (day 112), Subject 015-005 had a potassium value of 2.5 at the Day 14, Subject 018-001 had a potassium value of 2.2 at the week 12 (day 84, not shown in table below), (Etiology Groups 1 and 2 (N=47)

TABLE 14

Number of Subjects with Potassium values <=3.5 mmol/L Etiology Groups 1 and 2 (N = 47)

| | Non-Hypokalemic >3.5 mmol/L | Hypokalemic <=3.5 mmol/L |
|---|---|---|
| Day 14 | 38 | 8 |
| Day 42 | 35 | 6 |
| Day 70 | 30 | 6 |
| Day 112 | 23 | 9 |
| Day 168 | 37 | 5 |
| Day 210 | 37 | 3 |

What is claimed is:

1. A method for reducing the risk of developing hypokalemia or preventing the development of hypokalemia in an adult patient with endogenous Cushing's syndrome having type 2 diabetes mellitus or glucose intolerance, wherein the patient will be treated with a glucocorticoid receptor modulator (GRM) to control hyperglycemia secondary to hypercortisolism, the method comprising:

Obtaining a potassium level and a morning cortisol level determined from a sample obtained from said patient: and then
(a) identifying an adult patient with endogenous Cushing's syndrome having type 2 diabetes mellitus or glucose intolerance who:
  (i) has greatly increased risk of developing hypokalemia with GRM treatment, said patient having a morning serum cortisol level that is at least 27 micrograms per deciliter (pg/dL),
  (ii) does not have a lower than normal potassium level;
  (iii) has not been administered a GRM, and
  (iv) will be treated with a GRM to control hyperglycemia secondary to hypercortisolism;
(b) administering to said identified patient an effective amount of a therapeutic agent for treating hypokalemia, and then
(c) administering to the identified patient an initial dose of GRM, whereby the identified patient is treated to control hyperglycemia secondary to hypercortisolism and the risk of developing hypokalemia is reduced or hypokalemia is prevented in the patient,
wherein said GRM is mifepristone.

2. The method of claim 1, wherein the patient suffers from ACTH-dependent Cushing's syndrome.

3. The method of claim 1, further comprising administering to the patient the therapeutic agent for treating hypokalemia just before, or at the same time as, increasing the patient's initial GRM dose and administering to the patent a second and higher dose of GRM.

4. The method of claim 1, wherein the therapeutic agent for treating hypokalemia comprises a mineralocorticoid receptor antagonist or a potassium supplement.

5. The method of claim 4, wherein the mineralocorticoid receptor antagonist is spironolactone.

6. The method of claim 1, wherein the initial GRM dose is 300 mg/day, 600 mg/day, 900 mg/day, or 1200 mg/day of mifepristone.

7. The method of claim 1, wherein the patient has failed surgery, or is not a candidate for surgery, for Cushing's syndrome.

* * * * *

UNITED STATES PATENT AND TRADEMARK OFFICE
CERTIFICATE OF CORRECTION

PATENT NO. : 10,780,097 B2
APPLICATION NO. : 16/109585
DATED : September 22, 2020
INVENTOR(S) : Andreas Moraitis Page 1 of 1

It is certified that error appears in the above-identified patent and that said Letters Patent is hereby corrected as shown below:

In the Claims

In Column 47, Claim 1, Line 18, delete "(pg/dL)" and replace with --(µg/dL)--

In Column 48, Claim 3, Line 12, delete "patent" and replace with --patient--

Signed and Sealed this
Tenth Day of November, 2020

Andrei Iancu
*Director of the United States Patent and Trademark Office*